(12) United States Patent
Huang et al.

(10) Patent No.: US 11,584,731 B2
(45) Date of Patent: Feb. 21, 2023

(54) SALT OF CYCLOHEXANE DERIVATIVE

(71) Applicants: SHANGHAI JINGXIN BIOLOGY & PHARMACEUTICAL CO., LTD, Shanghai (CN); ZHEJIANG JINGXIN PHARMACEUTICAL CO., LTD., Zhejiang (CN)

(72) Inventors: Yue Huang, Zhejiang (CN); Fei Zheng, Zhejiang (CN); Xiaoyun Fu, Zhejiang (CN); Chunlan Tang, Zhejiang (CN); Dan Zhu, Zhejiang (CN)

(73) Assignees: Shanghai Jingxin Biology & Pharmaceutical Co., Ltd, Shanghai (CN); Zhejiang Jingxin Pharmaceutical Co., Ltd., Shaoxing (CN)

( * ) Notice: Subject to any disclaimer, the term of this patent is extended or adjusted under 35 U.S.C. 154(b) by 0 days.

(21) Appl. No.: 17/267,160

(22) PCT Filed: Aug. 13, 2019

(86) PCT No.: PCT/CN2019/100366
§ 371 (c)(1),
(2) Date: Feb. 9, 2021

(87) PCT Pub. No.: WO2020/042903
PCT Pub. Date: Mar. 5, 2020

(65) Prior Publication Data
US 2021/0309631 A1    Oct. 7, 2021

(30) Foreign Application Priority Data

| Aug. 30, 2018 | (CN) | 201811006909.2 |
| Aug. 30, 2018 | (CN) | 201811007027.8 |
| Aug. 30, 2018 | (CN) | 201811007871.0 |
| Aug. 30, 2018 | (CN) | 201811009030.3 |

(51) Int. Cl.
*C07D 333/66* (2006.01)
*A61K 31/496* (2006.01)
*C07D 409/04* (2006.01)

(52) U.S. Cl.
CPC .......... *C07D 333/66* (2013.01); *A61K 31/496* (2013.01); *C07D 409/04* (2013.01)

(58) Field of Classification Search
CPC .................................................. C07D 333/66
See application file for complete search history.

(56) References Cited

U.S. PATENT DOCUMENTS 10,301,277 B2 *   5/2019  Huang ................. A61K 9/2018

FOREIGN PATENT DOCUMENTS

| CN | 106518841 | 3/2017 |
| WO | WO-2017/045599 | 3/2017 |

OTHER PUBLICATIONS

Eric R. Marcotte J "Animal models of schizophrenia: a critical review" Psychiatry Neurosci 2001;26(5):395-410.*
Kakkar "Management of Parkinson's disease: Current and future pharmacotherapy" European Journal of Pharmacology 750 (2015) 74-81.*
Adam, Octavian R. "Symptomatic Treatment of Huntington Disease" Neurotherapeutics: The Journal of the American Society for Experimental NeuroTherapeutics Apr. 2008, vol. 5, 181-197.*
Newman "Solid form changes during drug development: good, bad, and ugly case studies" AAPS Open (2016) 2:2, 1-11.*
International Search Report dated Nov. 21, 2019 issued in International Application No. PCT/CN2019/100366, with English translation, 8 pages.

* cited by examiner

*Primary Examiner* — David K O'Dell
(74) *Attorney, Agent, or Firm* — Foley & Lardner LLP

(57) ABSTRACT

The present invention provides a maleate, phosphate, sulfate, hydrochloride of a cyclohexane derivative, N'-[trans-4-[2-[7-(benzo[b]thiophene)-7-piperazinyl]ethyl]cyclohexyl]-N,N-dimethylurea, as shown in Formula I and crystal forms thereof. The crystal forms have low hygroscopicity and good stability and are convenient for long-term storage and transportation; or the crystal forms have a long half-life in vivo, high bioavailability and small individual difference, and thus have obvious clinical application advantages.

8 Claims, 22 Drawing Sheets

SALT OF CYCLOHEXANE DERIVATIVE

CROSS-REFERENCE TO RELATED APPLICATIONS

The present application is a 371 of PCT/CN2019/100366, filed Aug. 13, 2019, which is based upon and claims priority to Chinese patent application CN201811006909.2, filed on Aug. 30, 2018, Chinese patent application CN201811007027.8, filed on Aug. 30, 2018, Chinese patent application CN201811007871.0, filed Aug. 30, 2018, and Chinese patent application CN201811009030.3, filed Aug. 30, 2018, each of which are incorporated herein by reference in their entireties.

TECHNICAL FIELD

The present invention belongs to the field of medicinal chemistry, and particularly relates to a cyclohexane derivative salt for treating mental diseases and a preparation method thereof.

BACKGROUND OF THE INVENTION

The present inventors have disclosed in CN 106518841A a compound 1 of Formula I having the chemical name N'-[trans-4-[2-[7-(benzo[b]thiophene)-7-piperazinyl]ethyl] cyclohexyl]-N,N-dimethylurea. A cyclohexane derivative N'-[trans-4-[2-[7-(benzo[b]thiophene)-7-piperazinyl]ethyl] cyclohexyl]-N,N-dimethylurea as shown in Formula I has D2/D3 antagonist effect, 5-hydroxytryptamine absorption inhibition effect and anti-schizophrenic effect, and particularly has high D3/D2 receptor selectivity and small side effect,

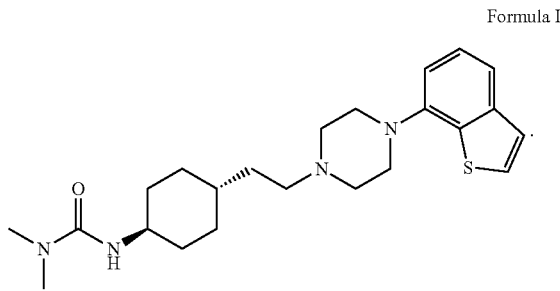 [SMILES: CN(C)C(=O)N[C@H]1CC[C@H](CCN2CCN(c3cccc4ccsc34)CC2)CC1]

Formula I

In order to improve the stability of the compound during formulation as well as during storage and to improve the pharmacokinetic properties of the compound, a more advantageous compound form is required, such as a salt of a compound of Formula I.

SUMMARY

Based on the existing compound of the Formula I, through intensive research, the inventor develops the following salts of the compound of following Formula I, which improve the stability of the compound I and reduce the hygroscopicity of the compound I, and the experiment in vivo proves that the half-life in vivo is longer, the bioavailability in vivo is higher, and the individual difference in vivo is small. Specifically, the present invention provides the following technical solutions.

A first aspect of the present invention provides a salt of the cyclohexane derivative N'-[trans-4-[2-[7-(benzo[b]thiophene)-7-piperazinyl]ethyl]cyclohexyl]-N,N-dimethylurea of Formula I, wherein the salt comprises an anion which is a maleate ion,

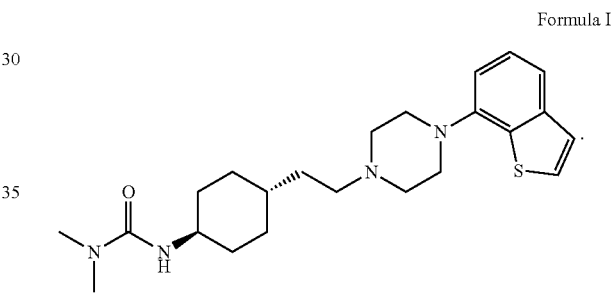

Formula I

In one embodiment, in the maleate of the present invention, the stoichiometric ratio of the compound of Formula I to the anion is 1:1.

In one embodiment, in the maleate of the present invention, the chemical formula of the maleate of the compound of Formula I is as shown in Formula II,

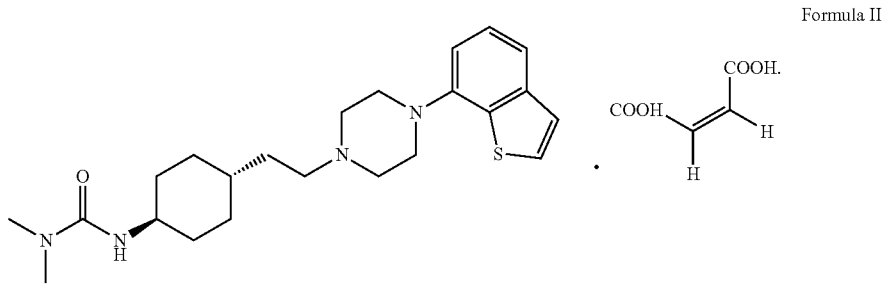 [SMILES: CN(C)C(=O)N[C@H]1CC[C@H](CCN2CCN(c3cccc4ccsc34)CC2)CC1 ; O=C(O)/C=C\C(=O)O]

Formula II

In one embodiment, the X-ray powder diffraction pattern of the maleate of the present invention, expressed in 2θ angle by using Cu-Kα radiation, has diffraction peaks at least at 11.804°±0.2°, 12.703°±0.2°, 13.493°±0.2°, 14.495°±0.2°, 15.096°±0.2°, 17.108°±0.2°, 19.104°±0.2°, 19.655°±0.2°, 20.023°±0.2°, 21.611°±0.2° and 24.088°±0.2°; preferably, has diffraction peaks at least at 11.804°±0.02°, 12.703°±0.02°, 13.493°±0.02°, 14.495°±0.02°, 15.096°±0.02°, 17.108°±0.02°, 19.104°±0.02°, 19.655°±0.02°, 20.023°±0.02°, 21.611°±0.02° and 24.088°±0.02°. In one embodiment, the maleate of the present invention also has diffraction peaks at 2θ values of 7.246°±0.2°, 17.567°±0.2°, 18.794°±0.2°, 20.395°±0.2°, 21.030°±0.2°, 22.496°±0.2°, 24.867°±0.2° and 26.412°±0.2°; preferably, also has diffraction peaks at 2θ values of 7.246°±0.02°, 17.567°±0.02°, 18.794°±0.02°, 20.395°±0.02°, 21.030°±0.02°, 22.496°±0.02°, 24.867°±0.02° and 26.412°±0.02°.

In one embodiment, the maleate of the present invention also has diffraction peaks at 2θ values of 11.045°±0.2°, 22.997°±0.2°, 25.336°±0.2°, 27.786°±0.2°, 28.292°±0.2°, 28.914°±0.2°, 29.804°±0.2°, 30.770°±0.2°, 31.628°±0.2° and 33.952°±0.2°; preferably, also has diffraction peaks at 2θ values of 11.045°±0.02°, 22.997°±0.02°, 25.336°±0.02°, 27.786°±0.02°, 28.292°±0.02°, 28.914°±0.02°, 29.804°±0.02°, 30.770°±0.02°, 31.628°±0.02° and 33.952°±0.02°. In one embodiment, the maleate of the present invention has an XRPD pattern as shown in FIG. 5A.

In one embodiment, the maleate of the present invention has an endothermic peak at 191.8° C. in DSC analysis.

In one embodiment, the maleate of the present invention has a DSC pattern as shown in FIG. 5B.

In one embodiment, the maleate of the present invention has a weight loss of up to 0.41% at 150° C. in TGA analysis.

In one embodiment, the maleate of the present invention has a TGA pattern as shown in FIG. 5C. The present invention also provides a method for preparing a maleate of a compound of Formula I, comprising the following step: reacting the compound of Formula I with maleic acid in an organic solvent to obtain a maleate of the compound of Formula I.

In one embodiment, in the maleate of the present invention, the compound of Formula I and maleic acid are reacted in a molar ratio of 1:1 to 1:2; preferably, the molar ratio is from 1:1 to 1:1.1.

In one embodiment, the organic solvent is selected from isopropanol, acetone, ethyl acetate, acetonitrile, toluene or a mixture of two or more thereof.

The invention also provides a pharmaceutical composition for the treatment or amelioration of schizophrenia, abalienation, mental disorders, abalienatio mentis, emotional disturbance, bipolar disorders, depression, phobia, obsessive compulsive disorders, anxiety disorders or cognitive disorders, wherein the pharmaceutical composition comprises the maleate and pharmaceutically acceptable auxiliaries.

The maleate of the compound of Formula I of the present invention has high crystallinity, low TGA weight loss, high and unique DSC endothermic signal; low hygroscopicity, good stability, and convenient long-term storage and transportation, thereby reducing the production cost; and it was proved by experiment in vivo that the bioavailability was high and the half-life was long, so it was an ideal salt for the compound of Formula I.

A second aspect of the present invention provides a salt of the cyclohexane derivative N'-[trans-4-[2-[7-(benzo[b]thiophene)-7-piperazinyl]ethyl]cyclohexyl]-N,N-dimethylurea of Formula I, wherein the salt comprises an anion which is a phosphate ion,

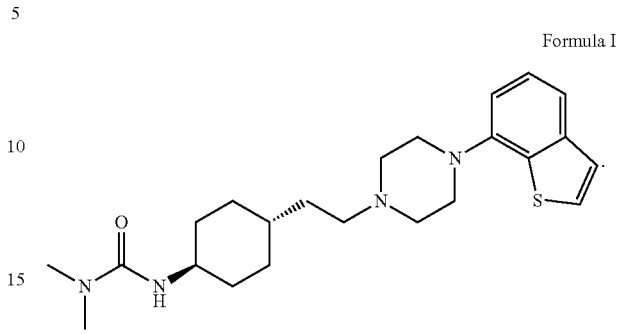

Formula I

In one embodiment, in the phosphate of the present invention, the stoichiometric ratio of the compound of Formula I to the anion is 1:1.

In one embodiment, in the phosphate of the present invention, the chemical formula of the phosphate of the compound of Formula I is as shown in Formula II-2, Formula II-2

·H$_3$PO$_4$.

In one embodiment, the X-ray powder diffraction pattern of the phosphate of the present invention, expressed in 2θ angle by using Cu-Kα radiation, has diffraction peaks at least at 13.986°±0.2°, 15.241°±0.2°, 15.844°±0.2°, 18.154°±0.2°, 21.005°±0.2°, 21.241°±0.2° and 21.811°±0.2°; preferably, has diffraction peaks at least at 13.986°±0.02°, 15.241°±0.02°, 15.844°±0.02°, 18.154°±0.02°, 21.005°±0.02°, 21.241°±0.02° and 21.811°±0.02°.

In one embodiment, the maleate of the present invention also has diffraction peaks at 2θ values of 6.794°±0.2°, 9.973°±0.2°, 19.990°±0.2°, 24.450°±0.2°, 26.019°±0.2°, 27.309°±0.2°, 30.710°±0.2°, 32.056°±0.2°, 35.718°±0.2° and 36.401°±0.2°; preferably, also has diffraction peaks at 2θ values of 6.794°±0.02°, 9.973°±0.02°, 19.990°±0.02°, 24.450°±0.02°, 26.019°±0.02°, 27.309°±0.02°, 30.710°±0.02°, 32.056°±0.02°, 35.718°±0.02° and 36.401°±0.02°.

In one embodiment, the XRPD pattern of the phosphate of the present invention is shown in FIG. 4A.

In one embodiment, the phosphate of the present invention has an endothermic peak at 213.9° C. in DSC analysis.

In one embodiment, the phosphate of the present invention has a DSC pattern as shown in FIG. 4B. In one embodiment, the phosphate of the present invention has a weight loss of up to 0.7% at 150° C. in TGA analysis.

In one embodiment, the phosphate of the present invention has a TGA pattern as shown in FIG. 4C. The present invention also provides a method for preparing a phosphate of a compound of Formula I, comprising the following step: reacting the compound of Formula I with phosphoric acid in an organic solvent to obtain a phosphate of the compound of Formula I.

In one embodiment, the compound of Formula I and phosphoric acid are reacted in a molar ratio of 1:1 to 1:2; preferably, the molar ratio is from 1:1 to 1:1.1.

In one embodiment, the organic solvent is selected from isopropanol, acetone, ethyl acetate, acetonitrile, toluene or a mixture of two or more thereof.

The invention also provides a pharmaceutical composition for the treatment or amelioration of schizophrenia, abalienation, mental disorders, abalienatio mentis, emotional disturbance, bipolar disorders, depression, phobia, obsessive compulsive disorders, anxiety disorders or cognitive disorders, wherein the pharmaceutical composition comprises the phosphate and pharmaceutically acceptable auxiliaries.

The phosphate of the compound of Formula I of the present invention has high crystallinity, low TGA weight loss, high and unique DSC endothermic signal, and it was proved by experiment in vivo that the bioavailability was high and the half-life was long, so it was an ideal salt for the compound of Formula I.

A third aspect of the present invention provides a salt of the cyclohexane derivative N'-[trans-4-[2-[7-(benzo[b]thiophene)-7-piperazinyl]ethyl]cyclohexyl]-N,N-dimethylurea of Formula I, wherein the salt comprises an anion which is a sulfate ion,

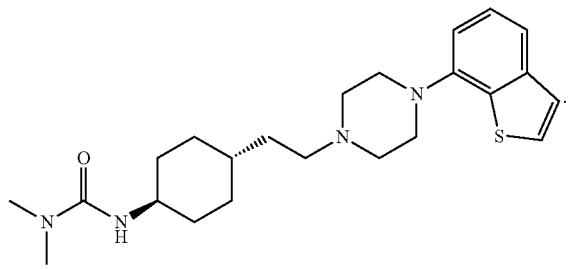

Formula I

In one embodiment, in the sulfate of the present invention, the stoichiometric ratio of the compound of Formula I to the anion is 1:1.

In one embodiment, the chemical formula of the sulfate of the present invention is as shown in Formula II-3,

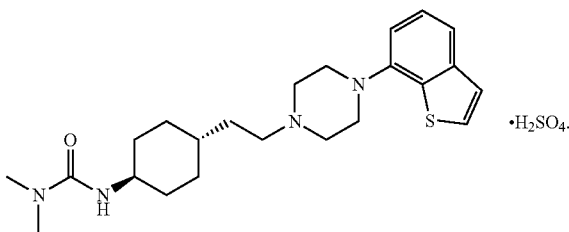

Formula II-3

In one embodiment, the X-ray powder diffraction pattern of the sulfate of the present invention, expressed in 2θ angle by using Cu-Kα radiation, has diffraction peaks at least at 6.719°±0.2°, 15.927°±0.2°, 17.257°±0.2°, 17.781°±0.2°, 18.294°±0.2°, 18.863°±0.2°, 21.464°±0.2°, 21.711°±0.2° and 23.806°±0.2°; preferably, has diffraction peaks at least at 6.719°±0.02°, 15.927°±0.02°, 17.257°±0.02°, 17.781°±0.02°, 18.294°±0.02°, 18.863°±0.02°, 21.464°±0.02°, 21.711°±0.02° and 23.806°±0.02°.

In one embodiment, the sulfate of the present invention also has diffraction peaks at 2θ values of 9.858°±0.2°, 14.437°±0.2°, 15.240°±0.2°, 20.792°±0.2°, 23.204°±0.2° and 27.023°±0.2°; preferably, also has diffraction peaks at 2θ values of 9.858°±0.02°, 14.437°±0.02°, 15.240°±0.02°, 20.792°±0.02°, 23.204°±0.02° and 27.023°±0.02°.

In one embodiment, the sulfate of the present invention also has diffraction peaks at 2θ values of 7.195°±0.2°, 7.947°±0.2°, 12.610°±0.2°, 13.414°±0.2°, 14.823°±0.2°, 20.187°±0.2°, 22.207°±0.2°, 22.741°±0.2°, 24.552°±0.2°, 25.532°±0.2°, 26.631°±0.2°, 27.515°±0.2°, 28.190°±0.2°, 28.563°±0.2°, 29.829°±0.2°, 32.993°±0.2°, 34.360°±0.2° and 36.462°±0.2°; preferably, has diffraction peaks at 2θ values of 7.195°±0.02°, 7.947°±0.02°, 12.610°±0.02°, 13.414°±0.02°, 14.823°±0.02°, 20.187°±0.02°, 22.207°±0.02°, 22.741°±0.02°, 24.552°±0.02°, 25.532°±0.02°, 26.631°±0.02°, 27.515°±0.02°, 28.190°±0.02°, 28.563°±0.02°, 29.829°±0.02°, 32.993°±0.02°, 34.360°±0.02° and 36.462°±0.02°.

In one embodiment, the sulfate of the present invention has an XRPD pattern as shown in FIG. 3A. In one embodiment, the sulfate of the present invention has an endothermic peak at 195.1° C. in DSC analysis.

In one embodiment, the sulfate of the present invention has a DSC pattern as shown in FIG. 3B.

In one embodiment, the sulfate of the present invention has a weight loss of up to 0.43% at 150° C. in TGA analysis.

In one embodiment, the TGA pattern of the sulfate of the present invention is as shown in FIG. 3C. The present invention also provides a method for preparing a sulfate of the compound of Formula I, comprising the following step: reacting the compound of Formula I with sulphuric acid in an organic solvent to obtain a sulfate of the compound of Formula I.

In one embodiment, the compound of Formula I and sulphuric acid are reacted in a molar ratio of 1:1 to 1:2; preferably, the molar ratio is from 1:1 to 1:1.1.

In one embodiment, the organic solvent is selected from isopropanol, ethyl acetate, acetonitrile, toluene or a mixture of two or more thereof.

The invention also provides a pharmaceutical composition for the treatment or amelioration of schizophrenia, abalienation, mental disorders, abalienatio mentis, emotional disturbance, bipolar disorders, depression, phobia, obsessive compulsive disorders, anxiety disorders or cognitive disorders, wherein the pharmaceutical composition comprises the sulfate and pharmaceutically acceptable auxiliaries.

The sulfate of the compound of Formula I of the present invention has high crystallinity, low TGA weight loss, high and unique DSC endothermic signal, and has been proved by experiment in vivo that the effect is fast and the bioavailability is high.

A fourth aspect of the present invention provides a salt of the N'-[trans-4-[2-[7-(benzo[b]thiophene)-7-piperazinyl] ethyl]cyclohexyl]-N,N-dimethylurea of Formula I, wherein the salt comprises an anion which is a chloride ion, Formula I

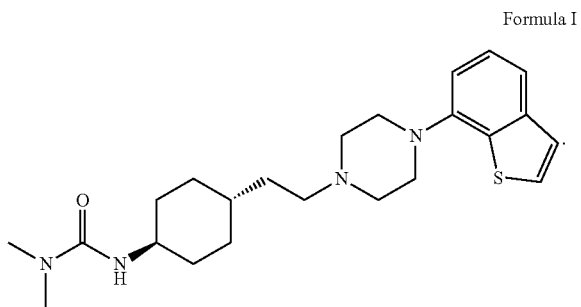 [SMILES: CN(C)C(=O)N[C@H]1CC[C@H](CCN2CCN(c3cccc4ccsc34)CC2)CC1]

In one embodiment, in the hydrochloride salt of the present invention, the stoichiometric ratio of the compound of Formula I to the anion is 1:1.

In one embodiment, the chemical formula of the hydrochloride salt of the present invention is as shown in Formula II-4, Formula II-4

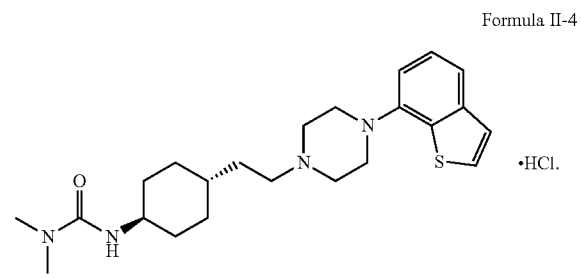 [SMILES: CN(C)C(=O)N[C@H]1CC[C@H](CCN2CCN(c3cccc4ccsc34)CC2)CC1]

·HCl

In one embodiment, the X-ray powder diffraction pattern of the hydrochloride salt of the present invention, expressed in 2θ angle by using Cu-Kα radiation, has diffraction peaks at least at 4.576°±0.2°, 10.982°±0.2°, 13.040°±0.2°, 13.738°±0.2°, 15.800°±0.2°, 16.914°±0.2°, 18.339°±0.2°, 19.119°±0.2°, 19.746°±0.2°, 20.029°±0.2°, 20.682°±0.2° and 23.570°±0.2°; preferably, has diffraction peaks at least at 4.576°±0.02°, 10.982°±0.02°, 13.040°±0.02°, 13.738°±0.02°, 15.800°±0.02°, 16.914°±0.02°, 18.339°±0.02°, 19.119°±0.02°, 19.746°±0.02°, 20.029°±0.02°, 20.682°±0.02° and 23.570°±0.02°.

In one embodiment, the hydrochloride salt of the present invention also has diffraction peaks at 2θ values of 9.123°±0.2°, 11.903°±0.2°, 12.216°±0.2°, 15.024°±0.2°, 17.370°±0.2°, 21.802°±0.2°, 22.151°±0.2°, 22.947°±0.2°, 24.581°±0.2°, 24.984°±0.2°, 25.586°±0.2°, 26.251°±0.2°, 26.533°±0.2°, 27.495°±0.2°, 30.408°±0.2° and 32.725°±0.2°; preferably, has diffraction peaks at 2θ values of 9.123°±0.02°, 11.903°±0.02°, 12.216°±0.02°, 15.024°±0.02°, 17.370°±0.02°, 21.802°±0.02°, 22.151°±0.02°, 22.947°±0.02°, 24.581°±0.02°, 24.984°±0.02°, 25.586°±0.02°, 26.251°±0.02°, 26.533°±0.02°, 27.495°±0.02°, 30.408°±0.02° and 32.725°±0.02°.

In one embodiment, the XRPD pattern of the hydrochloride salt of the present invention is as shown in FIG. 2A.

In one embodiment, the hydrochloride salt of the present invention has one endothermic peak at 278.2° C. in DSC analysis.

In one embodiment, the hydrochloride salt of the present invention has a DSC pattern as shown in FIG. 2B.

In one embodiment, the hydrochloride salt of the present invention has a weight loss of up to 0.49% at 150° C. in TGA analysis.

In one embodiment, the hydrochloride salt of the present invention has a TGA pattern as shown in FIG. 2C.

The present invention also provides a method for preparing a hydrochloride salt of the compound of Formula I, comprising the following step: reacting the compound of Formula I with hydrochloric acid in an organic solvent to obtain a hydrochloride salt of the compound of Formula I.

In one embodiment, in the method for preparing a salt of the compound of Formula I above, the reaction molar ratio of the compound of Formula I to hydrochloric acid is from 1:1 to 1:2; preferably, the molar ratio is from 1:1 to 1:1.1.

In one embodiment, in the method for preparing a salt of the compound of Formula I above, the organic solvent is toluene.

The invention also provides a pharmaceutical composition for the treatment or amelioration of schizophrenia, abalienation, mental disorders, abalienatio mentis, emotional disturbance, bipolar disorders, depression, phobia, obsessive compulsive disorders, anxiety disorders or cognitive disorders, wherein the pharmaceutical composition comprises the hydrochloride salt and pharmaceutically acceptable auxiliaries.

The hydrochloride salt of the compound of Formula I is good in stability and low in hygroscopicity, and compared with other salts, the in-vivo research also finds that the hydrochloride salt is high in crystallinity, small in TGA weight loss, high and unique DSC endothermic signal, with long half-life in vivo compared with free base and other salts, and has obvious advantages.

DETAILED DESCRIPTION OF THE EMBODIMENTS

Figure 1:
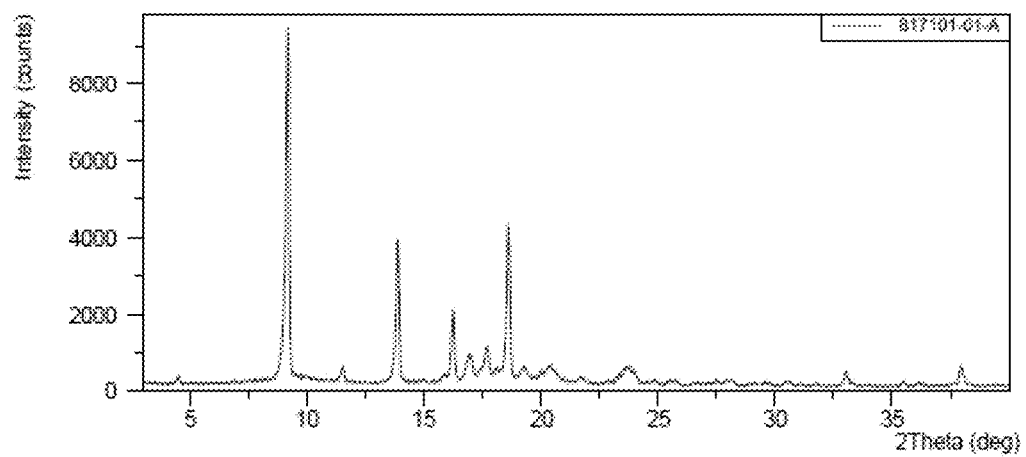
FIG. 1 is the X-ray powder diffraction pattern (XPRD pattern) of the free base of the compound of Formula I in one embodiment of the present invention.

The invention is further illustrated by the following embodiments. It is to be understood that these embodiments are for illustrative purposes only and are not intended to limit the invention. Various changes and modifications made by those skilled in the art based on the concept of the present invention should fall within the protection scope of the present invention.

The X-ray powder diffraction patterns of crystal forms of the various salts of N'-[trans-4-[2-[7-(benzo[b]thiophene)-7-piperazinyl]ethyl]cyclohexyl]-N,N-dimethylurea of the present invention, are expressed as diffraction peak positions, i.e., diffraction angle 2θ (°), interplanar spacing d (Å), Diffraction peak relative intensity (I/I0).

The term "relative intensity" refers to the ratio of the intensity of the other peak to the intensity of the highest intensity peak when the intensity of the highest intensity peak of all diffraction peaks of the X-ray powder diffraction pattern is 100%.

The term "substantially the same" means that at least 70%, at least 80%, at least 90%, at least 95%, or at least 99% of the peaks in the X-ray powder diffraction pattern appear in the given example X-ray powder diffraction pattern.

EXAMPLES

Reagents: the reactants and the catalyst used in the embodiment of the invention are chemical pure, and can be directly used or simply purified as required; The organic solvents and the like are all analytical reagent and are directly used. All reagents were purchased from Sinopharm Chemical Reagent Co., Ltd (Group) in Shanghai.

The amorphous form of the compound of Formula I is prepared according to the methods reported in the literature, e.g. in Example 5 of CN 106518841A, and is not limited thereto.

X-Ray Powder Diffraction:

X-ray powder diffraction analysis was performed on an X-ray powder diffractometer manufactured by PANalytacal using Cu-Kα radiation, testing a continuous scan of θ-2θ with a power of 45 kV×40 mA, a step width of 0.02°, and a scan range of 3-40° (2θ).

Differential Scanning Calorimetry (DSC) Characterization:

using TA Q2000/2500 differential scanning calorimeter to determine under the condition that the protective gas is nitrogen, the heating rate is 10° C./min, and the temperature rises gradually from 25° C. to the end point.

Thermogravimetric Analysis (TGA):

using TA Q5000/5500 thermal gravimetric analyzer to determine under the condition that the protective gas is nitrogen, the heating rate is 10° C./min, and the temperature rises gradually from room temperature to the end point.

Content Detection Method (HPLC):
Chromatographic Conditions

| Chromatographic column type | Agilent Eclipse Plus C18 4.6 * 100 mm, 3.5 μm | | |
|---|---|---|---|
| Mobile phase A | 0.1% FA (formic acid) aqueous solution | | |
| Mobile phase B | MeOH | | |
| Column temperature (° C.) | 40 | Flow rate (ml/min) | 1.0 |
| Detection wavelength (nm) | 260 | Sample injection amount | 10 μl |
| Specimen disc temperature (° C.) | Room temperature | | |

| Running gradient | | |
|---|---|---|
| Time (min) | Mobile phase A (%) | Mobile phase B (%) |
| 0 | 90 | 10 |
| 25 | 10 | 90 |
| 30 | 10 | 90 |
| 30.1 | 90 | 10 |
| 40 | 90 | 10 |

Solution Preparation

Diluent (blank solution): acetonitrile/water=1/1 (V/V)

Test sample solution: 5 mg of the sample was precisely weighed and placed in a 10 ml flask, dissolved with 2 ml of methanol and mixed with diluent (blank solution) at a constant volume to obtain.

Ion Chromatograph Test (IC) Conditions (Salt Formation Molar Ratio Test):

| Ion chromatograph | ThermoFisher ICS-1100 |
|---|---|
| Chromatographic column | IonPac AS18 Analytical Column, 250 * 4 mm |
| Mobile phase | 25 mM NaOH |
| Sample injection volume | 25 μL |
| Flow rate | 1.0 mL/min |
| Temperature/°C | 35° C. |
| Column temperature | 35° C. |
| Electric current | 80 mA |
| Run Time | The chloride ion was 6.0 min, the sulfate ion was 8.0 min, the bromide ion was 8.0 min, and the phosphate ion was 12.0 min |

Example 1: Preparation and Identification of Crystal Form a of the Free Base of N'-[trans-4-[2-[7-(benzo[b]thiophene)-7-piperazinyl]ethyl]cyclohexyl]-N,N-dimethylurea (Compound of Formula I)

The free base was prepared according to Example 5 of CN106518841A.

Preparation of 1-benzo[b]thiophene-4-piperazine hydrochloride

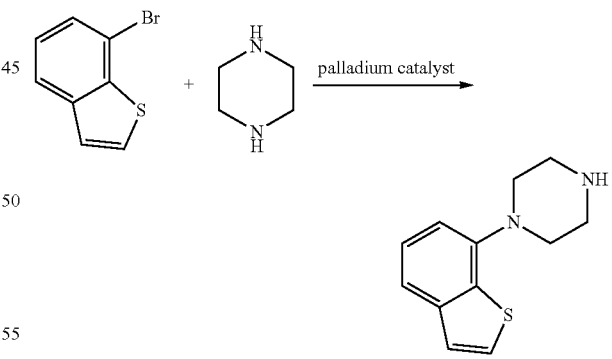

A mixture of 7.20 g of 7-bromobenzo[b]thiophene, 19.9 g of piperazine anhydride, 4.70 g of sodium tert-butoxide, 0.32 g of (R)-(+)-2,2'-bis (diphenylphosphino)-1,1'-dinaphthyl (BINAP), 0.63 g of dipalladium tris (dibenzylideneacetone) and 150 ml of toluene was refluxed under a nitrogen atmosphere for 1 h. 150 ml of water was poured into the reaction solution, then extracted with ethyl acetate (100 ml×3), washed with water, dried over anhydrous magnesium sulfate, and allowed to evaporate the solvent under reduced pressure (0.01 MPa, 45° C.). The residue was purified by silica gel column chromatography (dichloromethane:methanol:25% aqueous ammonia=100:10:1) to yield 4.60 g of 1-benzo[b]thiophen-4-yl-piperazine in the form of yellow oil. 2 ml of concentrated hydrochloric acid was added to a methanol solution (25 ml) containing 4.6 g of 1-benzo[b]thiophen-4-yl-piperazine, and the solvent was evaporated under reduced pressure (0.01 MPa, 45° C.). Ethyl acetate (50 ml) was added to the residue and the precipitated crystals were filtered, dissolved at reflux in 15 ml of methanol and then cooled to room temperature (25° C.) to recrystallize to obtain 1-benzo[b]thiophen-4-yl-piperazine hydrochloride in the form of colorless needles.

Preparation of tert-Butyl trans-4-[2-[7-(benzo[b]thiophene)-7-piperazinyl]ethyl]cyclohexyl-carbamate 2.54 g (10 mmol) of 1-benzo[b]thiophene-4-piperazine hydrochloride and 2.40 g (10 mmol) of trans-2-{1-[4-(N-tert-butoxycarbonyl) amino]cyclohexyl}-acetaldehyde were dissolved in 120 ml of dichloromethane, 1.40 ml (10 mmol) of triethylamine was added at room temperature (25° C.±2° C.) and stirred slowly for 10 min, then 3.16 g (14.8 mmol) of sodium triacetoxyborohydride was added gradually. The reaction proceeded for a further 24 h at room temperature under stirring, and after reaction, 120 ml of a 10% sodium bicarbonate solution was added. The reaction system was directly subjected to separation, the organic phase was dried over anhydrous sodium sulfate, and finally filtered and concentrated to dryness by rotary evaporation, and the solid was dissolved in 15 ml of ethyl acetate under reflux and cooled to room temperature (25° C.±2° C.) to crystallize to give 3.70 g of the desired product.

Preparation of trans-4-[2-[7-(benzo[b]thiophene)-7-piperazinyl]ethyl]cyclohexylamine

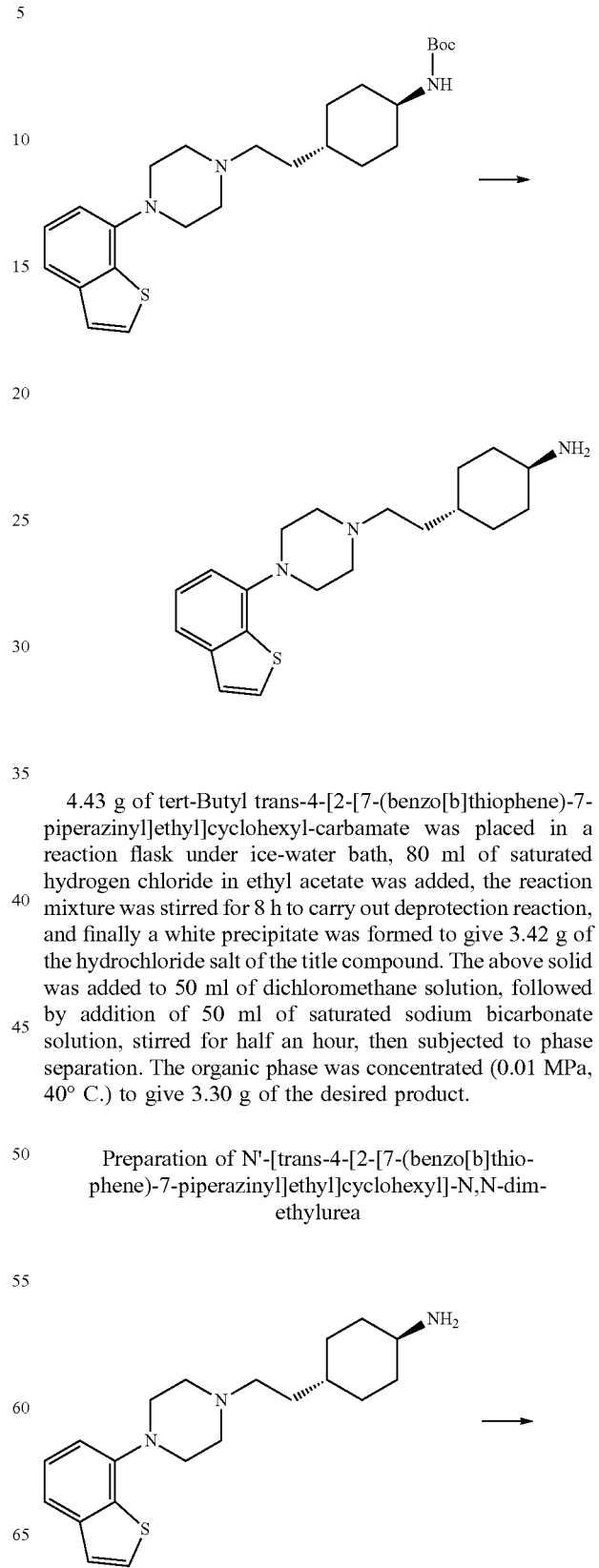

4.43 g of tert-Butyl trans-4-[2-[7-(benzo[b]thiophene)-7-piperazinyl]ethyl]cyclohexyl-carbamate was placed in a reaction flask under ice-water bath, 80 ml of saturated hydrogen chloride in ethyl acetate was added, the reaction mixture was stirred for 8 h to carry out deprotection reaction, and finally a white precipitate was formed to give 3.42 g of the hydrochloride salt of the title compound. The above solid was added to 50 ml of dichloromethane solution, followed by addition of 50 ml of saturated sodium bicarbonate solution, stirred for half an hour, then subjected to phase separation. The organic phase was concentrated (0.01 MPa, 40° C.) to give 3.30 g of the desired product.

Preparation of N'-[trans-4-[2-[7-(benzo[b]thiophene)-7-piperazinyl]ethyl]cyclohexyl]-N,N-dimethylurea -continued

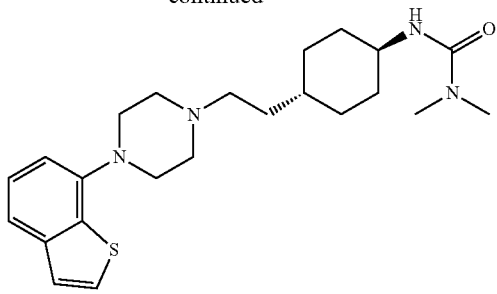

1.73 g of trans-4-[2-[7-(benzo[b]thiophene)-7-piperazinyl]ethyl]cyclohexylamine was dissolved in 50 ml of dichloromethane, followed by addition of 1.40 ml of triethylamine and 5.50 mmol of N, N-dimethylcarbamoyl chloride. The mixture was stirred for 48 h at room temperature (25° C.±2° C.). After reaction, 50 ml of water was added for extraction and the organic phase was concentrated (0.01 MPa, 45° C.), subjected to column chromatography (methanol:dichloromethane=1:10, 400 mesh silica gel) to collect the target fraction, which was concentrated to give 1.89 g of the amorphous desired product.

Preparation and Identification of Crystal Form a of the Free Base 200 mg of the above amorphous product was dissolved in ethyl acetated at reflux temperature of 77° C., cooled to room temperature (20-25° C.) and stirred for 1 h, filtered under suction and recrystallized to obtain a crystal form. It is designated as crystal Form A of the free base of the compound of Formula I, wherein the X-ray diffraction pattern (XRPD) is shown in FIG. 1; the solubility of the crystal Form A of the free base in water is about 0.031 mg/ml.

Example 2: Preparation and Identification of the Hydrochloride Salt of N'-[trans-4-[2-[7-(benzo[b]thiophene)-7-piperazinyl]ethyl]cyclohexyl]-N,N-dimethylurea (Compound of Formula I)

Preparation of hydrochloride salt: 200 mg of the free base product from Example 1 was mixed and stirred with 1.05 molar ratio of hydrochloric acid in toluene at room temperature for 3 days and dried under vacuum at 50° C. for 3 days to obtain the hydrochloride salt. It is in crystal form, designated as hydrochloride salt Form B of the compound of Formula I.

Figure 2A:
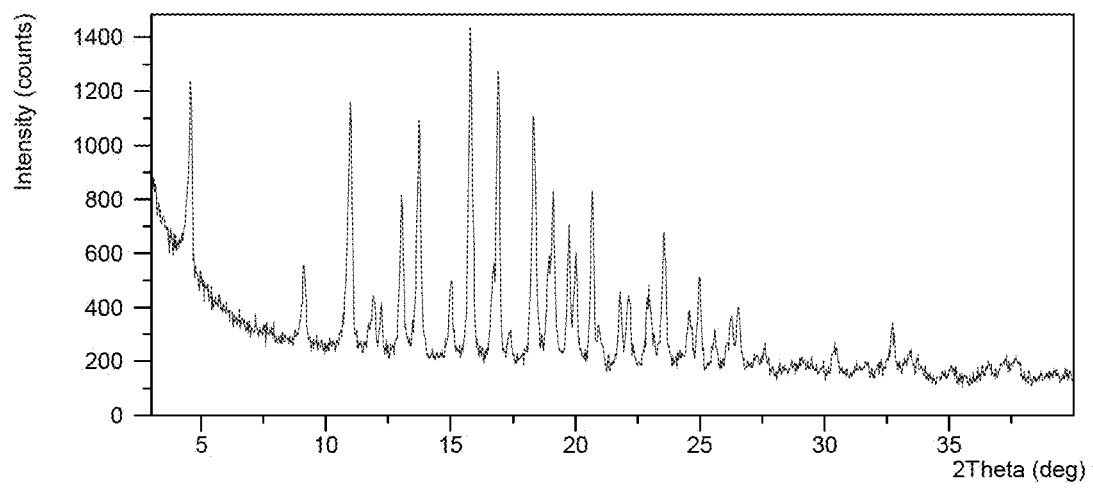
FIG. 2A is the X-ray powder diffraction pattern (XPRD pattern) of the hydrochloride salt of the compound of Formula I in one embodiment of the present invention.

FIG. 2A shows a powder X-ray diffraction pattern (XRPD) and the characteristic peaks for the corresponding spacing values (Å) at 2θ are provided in Table 1.

TABLE 1

XRPD Diffraction Peak Data for Hydrochloride Salt Form B

| Diffraction angle [° 2θ] | Interplanar spacing [Å] | Relative intensity [%] |
|---|---|---|
| 4.576941 | 19.30686 | 55.05 |
| 9.123195 | 9.69356 | 23.68 |
| 10.982470 | 8.05632 | 76.16 |
| 11.903470 | 7.43497 | 15.55 |
| 12.216890 | 7.24493 | 13.80 |
| 13.040680 | 6.78905 | 47.00 |
| 13.738740 | 6.44563 | 69.38 |
| 15.024150 | 5.89694 | 22.99 |
| 15.800660 | 5.60884 | 100.00 |

TABLE 1-continued

XRPD Diffraction Peak Data for Hydrochloride Salt Form B

| Diffraction angle [° 2θ] | Interplanar spacing [Å] | Relative intensity [%] |
|---|---|---|
| 16.914740 | 5.24185 | 85.20 |
| 17.370510 | 5.10532 | 7.84 |
| 18.339650 | 4.83767 | 73.96 |
| 19.119300 | 4.64212 | 49.76 |
| 19.746390 | 4.49609 | 40.83 |
| 20.029190 | 4.43324 | 32.41 |
| 20.682720 | 4.29462 | 50.63 |
| 21.802960 | 4.07643 | 19.48 |
| 22.151700 | 4.01303 | 20.51 |
| 22.947100 | 3.87570 | 22.56 |
| 23.570630 | 3.77457 | 40.16 |
| 24.581520 | 3.62158 | 15.53 |
| 24.984200 | 3.56412 | 27.39 |
| 25.586650 | 3.48155 | 10.42 |
| 26.251890 | 3.39482 | 15.34 |
| 26.533050 | 3.35948 | 19.10 |
| 27.495840 | 3.24399 | 3.76 |
| 30.408600 | 2.93957 | 7.54 |
| 32.725620 | 2.73655 | 14.39 |

Figure 2B:
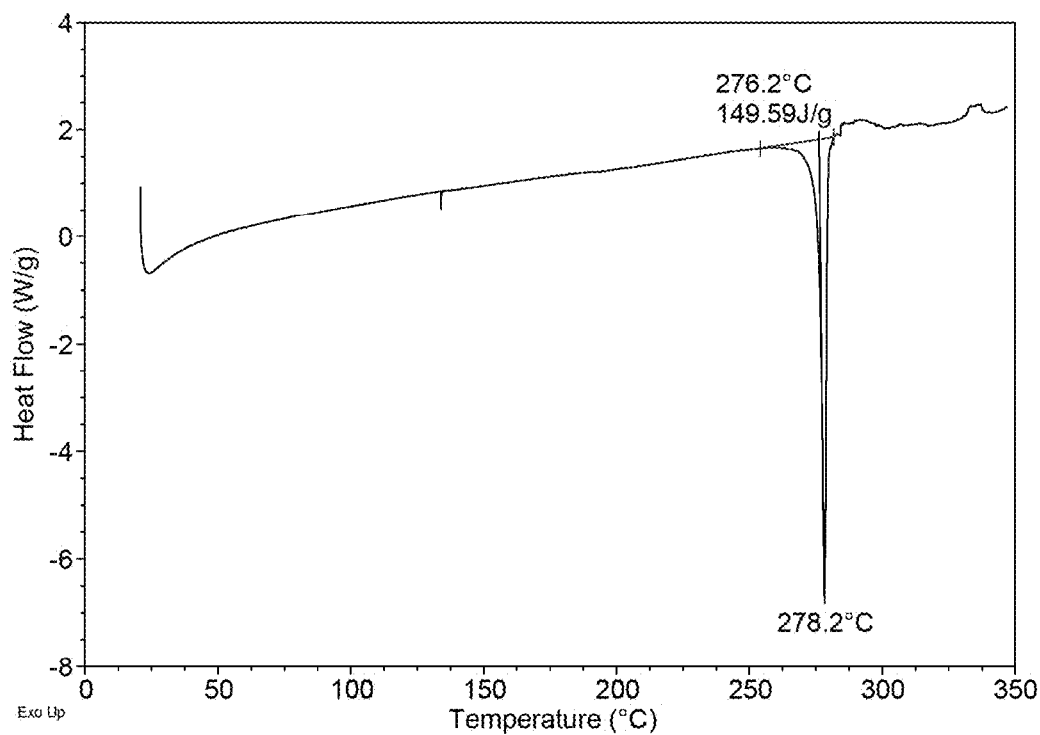
FIG. 2B is the differential scanning calorimetry pattern (DSC pattern) of the hydrochloride salt of the compound of Formula I in one embodiment of the present invention. The abscissa is temperature (° C.); the ordinate is the heat flux (W/g).
Figure 2C:
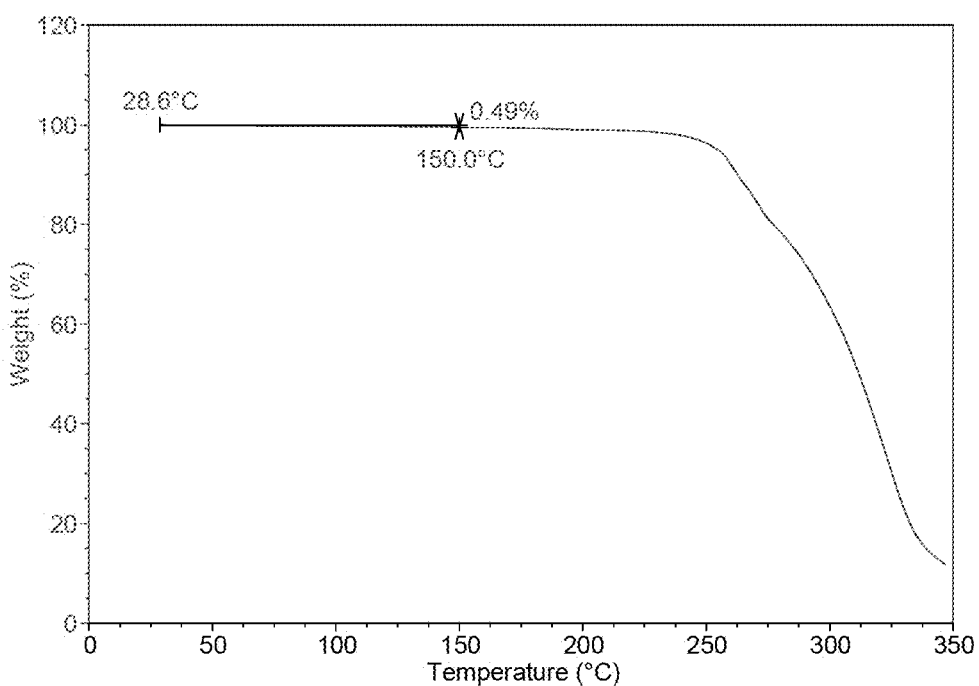
FIG. 2C is the thermogravimetric analysis (TGA pattern) of the hydrochloride salt of the compound of Formula I in one embodiment of the present invention.

For the hydrochloride salt Form B of the compound of Formula I, the solubility in water is greater than 4.6 mg/ml; the DSC results of FIG. 2B show that the sample has one endothermic peak at 278.2° C.; TGA of FIG. 2C shows that the sample has a 0.49% weight loss when heated to 150° C. HPLC/IC assays are consistent with a 1:1 stoichiometry (free base:hydrochloric acid).

Example 3: Preparation and Identification of the Sulfate of N'-[trans-4-[2-[7-(benzo[b]thiophene)-7-piperazinyl]ethyl]cyclohexyl]-N,N-dimethylurea (Compound of Formula I)

Preparation of the sulfate (a): 200 mg of the product from Example 1 was mixed and stirred with 1.05 molar ratio of sulfuric acid in ethyl acetate (EtOAc) at room temperature for 4 days, and dried under vacuum at 50° C. for 3 days to obtain the sulfate. It is in crystal form, designated as sulfate Form A of the compound of Formula I.

Figure 3A:
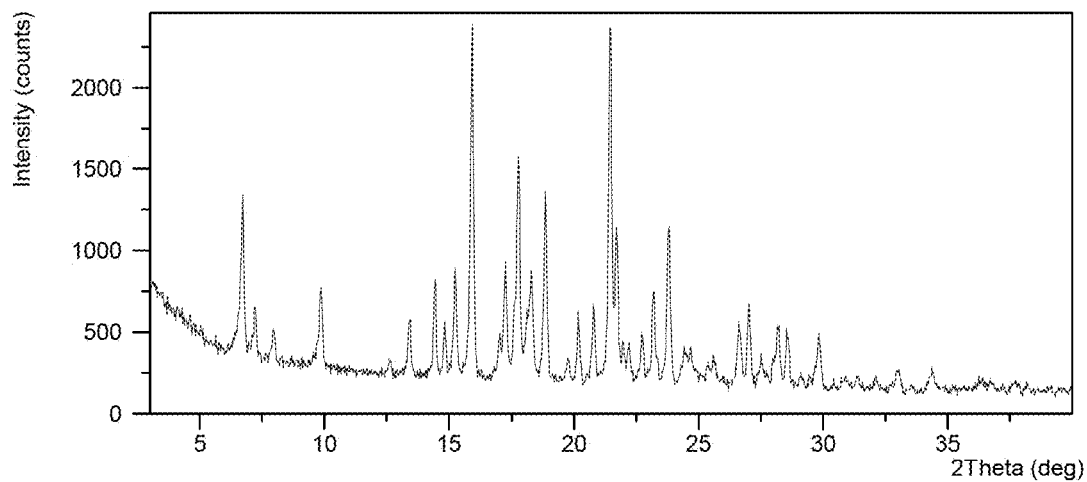
FIG. 3A is the X-ray powder diffraction pattern (XPRD pattern) of the sulfate of the compound of Formula I in one embodiment of the present invention.

FIG. 3A shows a powder X-ray diffraction pattern (XRPD) and the characteristic peaks for the corresponding spacing values (Å) at 2θ are provided in Table 2.

TABLE 2

XRPD Diffraction Peak Data for Sulfate Form A

| Diffraction angle [° 2θ] | Interplanar spacing [Å] | Relative intensity [%] |
|---|---|---|
| 6.719282 | 13.15520 | 44.09 |
| 7.195519 | 12.28556 | 10.70 |
| 7.947205 | 11.12514 | 7.24 |
| 9.858717 | 8.97195 | 21.50 |
| 12.610270 | 7.01979 | 3.93 |
| 13.414660 | 6.60062 | 15.56 |
| 14.437150 | 6.13535 | 26.09 |
| 14.823030 | 5.97649 | 13.36 |
| 15.240620 | 5.81366 | 28.09 |
| 15.927590 | 5.56443 | 99.41 |
| 17.257190 | 5.13859 | 31.62 |
| 17.781580 | 4.98822 | 61.09 |
| 18.294180 | 4.84959 | 30.33 |
| 18.863740 | 4.70443 | 53.45 |
| 20.187920 | 4.39875 | 17.60 |
| 20.792550 | 4.27218 | 20.94 |
| 21.464510 | 4.13993 | 100.00 |
| 21.711510 | 4.09339 | 40.36 |

TABLE 2-continued

XRPD Diffraction Peak Data for Sulfate Form A

| Diffraction angle [° 2θ] | Interplanar spacing [Å] | Relative intensity [%] |
|---|---|---|
| 22.207430 | 4.00309 | 10.20 |
| 22.741540 | 3.91027 | 12.81 |
| 23.204680 | 3.83326 | 24.80 |
| 23.806940 | 3.73763 | 43.59 |
| 24.552950 | 3.62573 | 7.64 |
| 25.532400 | 3.48883 | 5.35 |
| 26.631630 | 3.34727 | 17.27 |
| 27.023930 | 3.29956 | 21.99 |
| 27.515020 | 3.24178 | 7.32 |
| 28.190910 | 3.16557 | 16.24 |
| 28.563170 | 3.12516 | 14.00 |
| 29.829620 | 2.99530 | 14.63 |
| 32.993550 | 2.71494 | 4.90 |
| 34.360750 | 2.60998 | 5.11 |
| 36.462810 | 2.46419 | 1.68 |

Figure 3B:
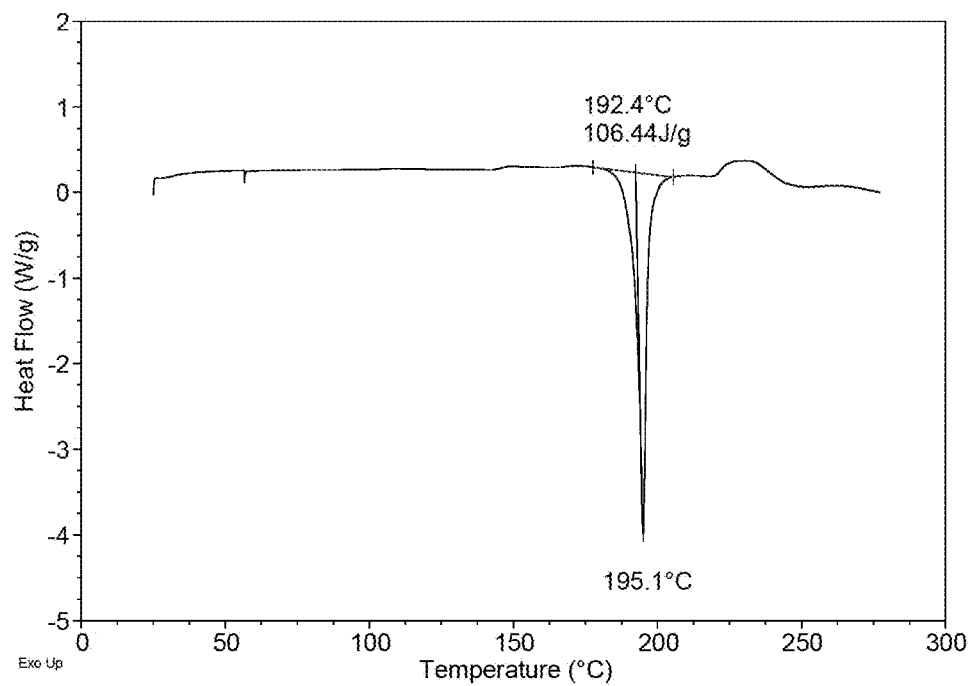
FIG. 3B is the differential scanning calorimetry pattern (DSC pattern) of the sulfate of the compound of Formula I in one embodiment of the present invention. The abscissa is temperature (° C.); the ordinate is the heat flux (W/g).
Figure 3C:
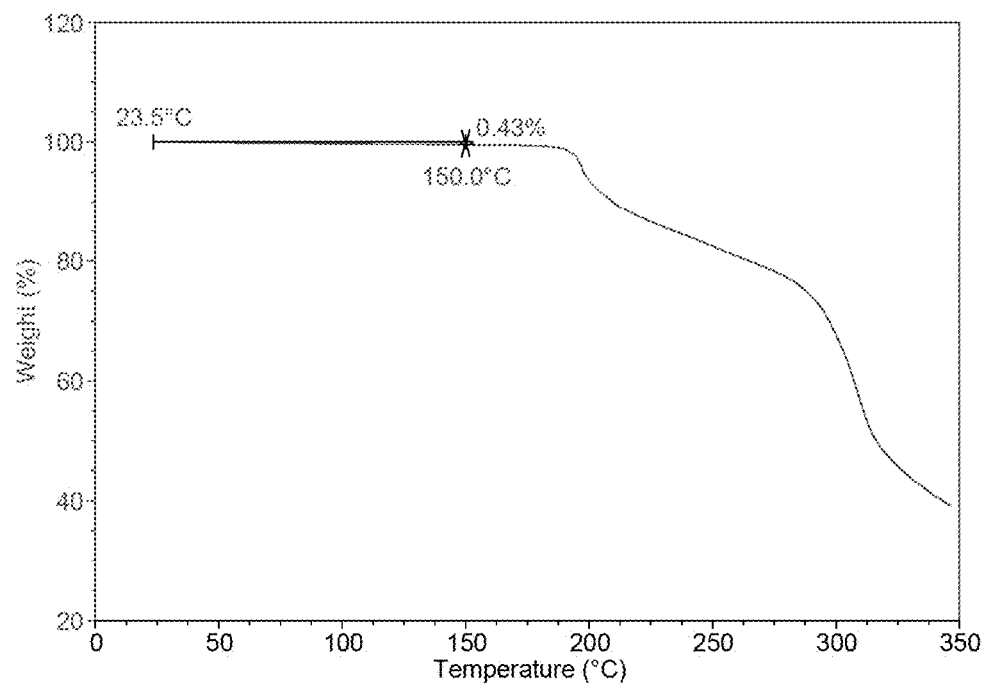
FIG. 3C is the thermogravimetric analysis pattern (TGA pattern) of the sulfate of the compound of Formula I in one embodiment of the present invention.

For the sulfate Form A of the compound of Formula I, the solubility in water is greater than 8.0 mg/ml; the DSC results of FIG. 3B show that the sample has one endothermic peak at 195.1° C.; TGA of FIG. 3C shows that the sample has a 0.43% weight loss when heated to 150° C. HPLC/IC assays are consistent with a 1:1 stoichiometry (free base:sulfuric acid).

Preparation of sulfate (b): 200 mg of the product from Example 1 was mixed and stirred with 1.05 molar ratio of sulfuric acid in isopropylamine (IPA) at room temperature for 4 days, and dried under vacuum at 50° C. for 3 days to obtain the sulfate, which is in crystal form and is substantially the same as the X-ray diffraction pattern (XRPD), DSC pattern and TGA pattern of the above sulfate Form A of the compound of Formula I.

Preparation of sulfate (c): 200 mg of the product from Example 1 was mixed and stirred with 1.05 molar ratio of sulfuric acid in acetonitrile (ACN) at room temperature for 4 days, and dried under vacuum at 50° C. for 3 days to obtain the sulfate, which is in crystal form and is substantially the same as the X-ray diffraction pattern (XRPD), DSC pattern and TGA pattern of the above sulfate Form A of the compound of Formula I.

Preparation of sulfate (d): 200 mg of the product from Example 1 was mixed and stirred with 1.05 molar ratio of sulfuric acid in methylbenzene (toluene) at room temperature for 4 days, and dried under vacuum at 50° C. for 3 days to obtain the sulfate, which is in crystal form and is substantially the same as the X-ray diffraction pattern (XRPD), DSC pattern and TGA pattern of the above sulfate Form A of the compound of Formula I.

Example 4: Preparation and Identification of the Phosphate of N'-[trans-4-[2-[7-(benzo[b]thiophene)-7-piperazinyl]ethyl]cyclohexyl]-N,N-dimethylurea (Compound of Formula I)

Preparation of phosphate (a): 200 mg of the product from Example 1 was mixed and stirred with 1.05 molar ratio of phosphoric acid in ethyl acetate (EtOAc) at room temperature for 5 days to obtain. It is in crystal form, designated as phosphate Form A of the compound of Formula I.

Figure 4A:
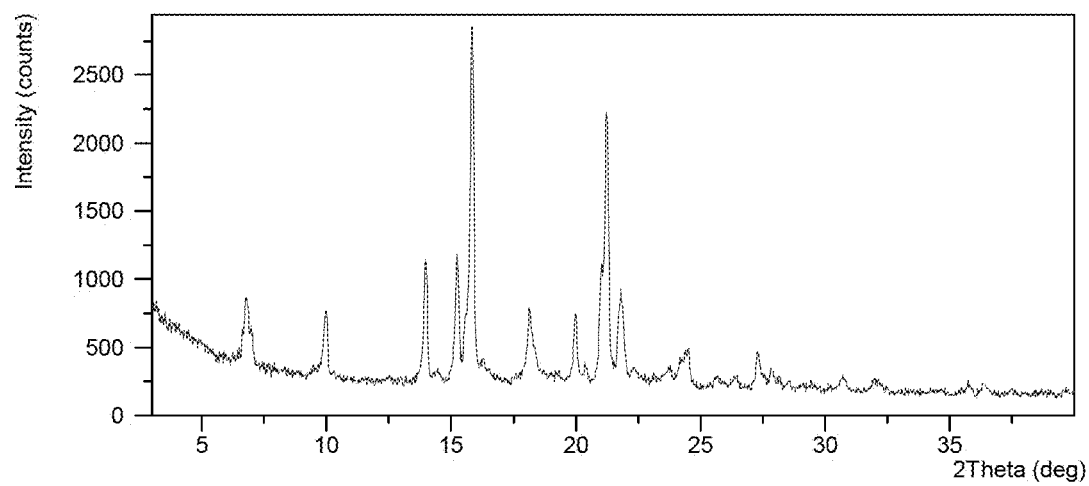
FIG. 4A is the X-ray powder diffraction pattern (XPRD pattern) of the phosphate of the compound of Formula I in one embodiment of the present invention.

FIG. 4A shows a powder X-ray diffraction pattern (XRPD) and the characteristic peaks for the corresponding spacing values (Å) at 2θ are provided in Table 3.

TABLE 3

XRPD Diffraction Peak Data for Phosphate Form A

| Diffraction angle [° 2θ] | Interplanar spacing [Å] | Relative intensity [%] |
|---|---|---|
| 6.794465 | 13.00980 | 18.09 |
| 9.973994 | 8.86852 | 17.67 |
| 13.986170 | 6.33215 | 33.04 |
| 15.241080 | 5.81349 | 33.97 |
| 15.844050 | 5.59358 | 100.00 |
| 18.154110 | 4.88669 | 20.98 |
| 19.990390 | 4.44176 | 19.30 |
| 21.005570 | 4.22933 | 30.57 |
| 21.241610 | 4.18287 | 75.24 |
| 21.811130 | 4.07492 | 26.04 |
| 24.450240 | 3.64073 | 8.99 |
| 26.019400 | 3.42462 | 0.62 |
| 27.309390 | 3.26572 | 9.19 |
| 30.710740 | 2.91134 | 3.58 |
| 32.056180 | 2.79215 | 2.76 |
| 35.718340 | 2.51383 | 2.08 |
| 36.401270 | 2.46822 | 2.60 |

Figure 4B:
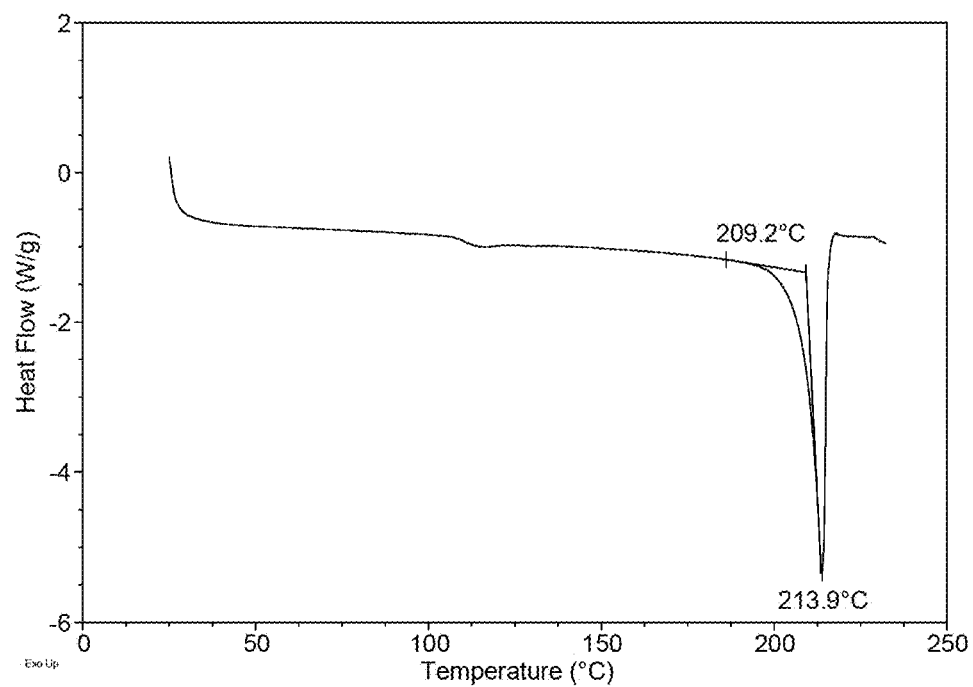
FIG. 4B is the differential scanning calorimetry pattern (DSC pattern) of the phosphate of the compound of Formula I in one embodiment of the present invention. The abscissa is temperature (° C.); the ordinate is the heat flux (W/g).
Figure 4C:
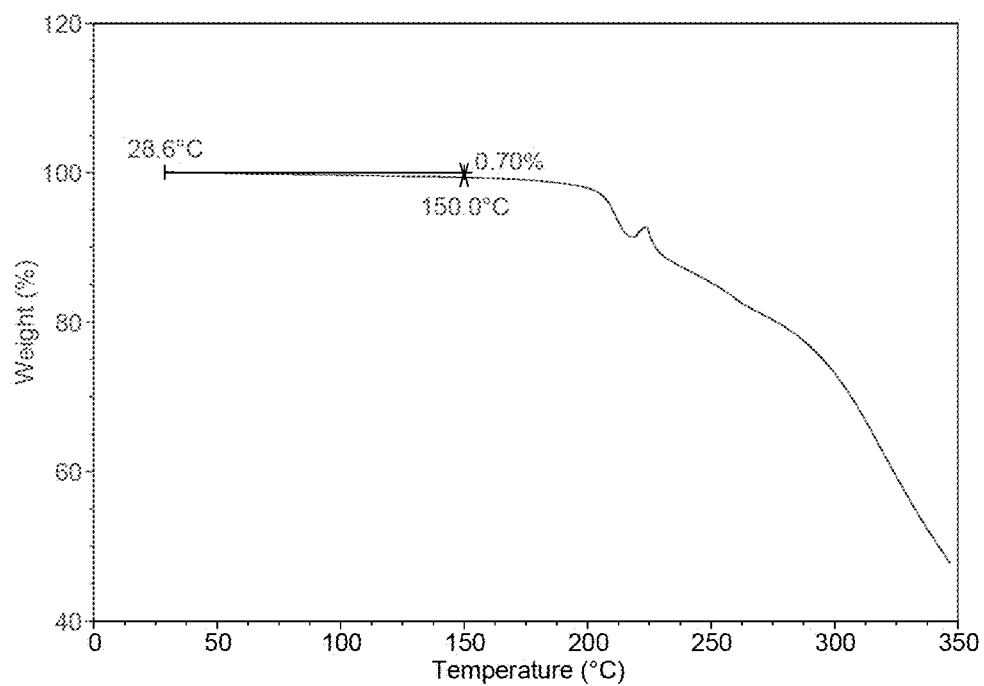
FIG. 4C is the thermogravimetric analysis (TGA pattern) of the phosphate of the compound of Formula I in one embodiment of the present invention.

For the phosphate Form A of the compound of Formula I, the solubility in water is greater than 7.6 mg/ml; the DSC results of FIG. 4B show that the sample has one endothermic peak at 213.9° C.; TGA of FIG. 4C shows that the sample has a 0.7% weight loss when heated to 150° C. Results of HPLC/IC assays are consistent with a 1:1 stoichiometry (free base:phosphoric acid).

Preparation of phosphate (b): 200 mg of the product from Example 1 was mixed and stirred with 1.05 molar ratio of phosphoric acid in isopropylamine (IPA) at room temperature for 5 days to obtain the phosphate, which is in crystal form and is substantially the same as the X-ray diffraction pattern (XRPD), DSC pattern and TGA pattern of the above phosphate Form A of the compound of Formula I.

Preparation of phosphate (c): 200 mg of the product from Example 1 was mixed and stirred with 1.05 molar ratio of phosphoric acid in acetone at room temperature for 5 days to obtain the phosphate, which is in crystal form and is substantially the same as the X-ray diffraction pattern (XRPD), DSC pattern and TGA pattern of the above phosphate Form A of the compound of Formula I.

Preparation of phosphate (d): 200 mg of the product from Example 1 was mixed and stirred with 1.05 molar ratio of phosphoric acid in acetonitrile (ACN) at room temperature for 5 days to obtain the phosphate, which is in crystal form, which is substantially the same as the X-ray diffraction pattern (XRPD), DSC pattern and TGA pattern of the phosphate crystal form A of the compound of Formula I.

Preparation of phosphate (e): 200 mg of the product from Example 1 was mixed and stirred with 1.05 molar ratio of phosphoric acid in methylbenzene (Toluene) at room temperature for 5 days to obtain the phosphate, which is in crystal form, which is substantially the same as the X-ray diffraction pattern (XRPD), DSC pattern and TGA pattern of the phosphate crystal form A of the compound of Formula I.

Example 5: Preparation and Identification of the Maleate of N'-[trans-4-[2-[7-(benzo[b]thiophene)-7-piperazinyl]ethyl]cyclohexyl]-N,N-dimethylurea (Compound of Formula I)

Preparation of maleate (a): 200 mg of the product from Example 1 was mixed and stirred with 1.05 molar ratio of maleic acid in acetone at room temperature for 5 days to obtain the maleate, which is in a crystal form, designated as maleate Form A of the compound of Formula I.

Figure 5A:
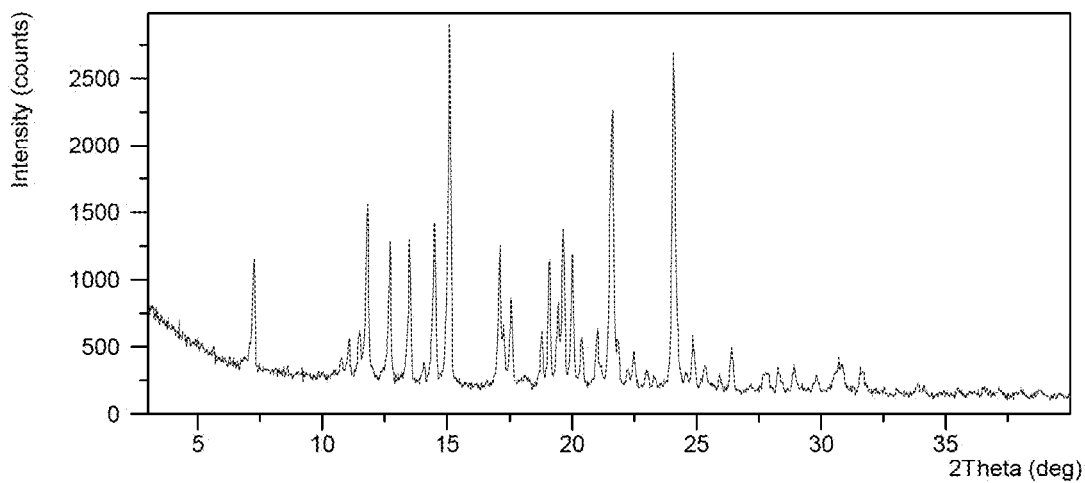
FIG. 5A is the X-ray powder diffraction pattern (XPRD pattern) of crystal Form A of the maleate of the compound of Formula I in one embodiment of the present invention.

FIG. 5A shows a powder X-ray diffraction pattern (XRPD) and the characteristic peaks for the corresponding spacing values (Å) at 2θ are provided in Table 4.

TABLE 4

XRPD Diffraction Peak Data for Maleate Form A

| Diffraction angle [° 2θ] | Interplanar spacing [Å] | Relative intensity [%] |
|---|---|---|
| 7.246772 | 12.19878 | 29.23 |
| 11.045240 | 8.01067 | 8.33 |
| 11.804630 | 7.49700 | 48.03 |
| 12.703730 | 6.96836 | 37.24 |
| 13.493910 | 6.56202 | 40.27 |
| 14.495010 | 6.11099 | 45.47 |
| 15.096910 | 5.86868 | 100.00 |
| 17.108350 | 5.18296 | 38.11 |
| 17.567560 | 5.04850 | 24.86 |
| 18.794690 | 4.72156 | 15.60 |
| 19.104540 | 4.64567 | 36.19 |
| 19.655590 | 4.51666 | 43.21 |
| 20.023940 | 4.43440 | 37.51 |
| 20.395360 | 4.35447 | 13.70 |
| 21.030950 | 4.22429 | 14.53 |
| 21.611370 | 4.11213 | 77.73 |
| 22.496370 | 3.95232 | 10.60 |
| 22.997610 | 3.86730 | 4.66 |
| 24.088590 | 3.69457 | 89.87 |
| 24.867140 | 3.58063 | 13.78 |
| 25.336430 | 3.51536 | 6.62 |
| 26.412080 | 3.37459 | 12.01 |
| 27.786650 | 3.21070 | 4.90 |
| 28.292510 | 3.15443 | 6.19 |
| 28.914740 | 3.08795 | 7.44 |
| 29.804120 | 2.99780 | 4.24 |
| 30.770440 | 2.90583 | 7.49 |
| 31.628070 | 2.82896 | 6.05 |
| 33.952110 | 2.64045 | 1.97 |

Figure 5B:
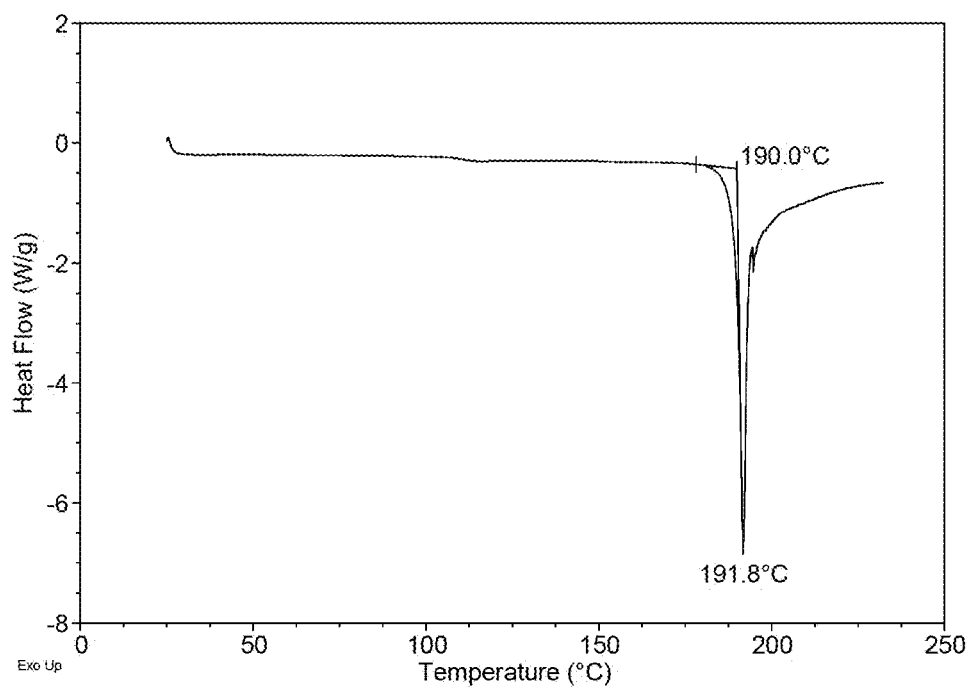
FIG. 5B is the differential scanning calorimetry pattern (DSC pattern) of crystal Form A of the maleate of the compound of Formula I in one embodiment of the present invention. The abscissa is temperature (° C.); the ordinate is the heat flux (W/g).
Figure 5C:
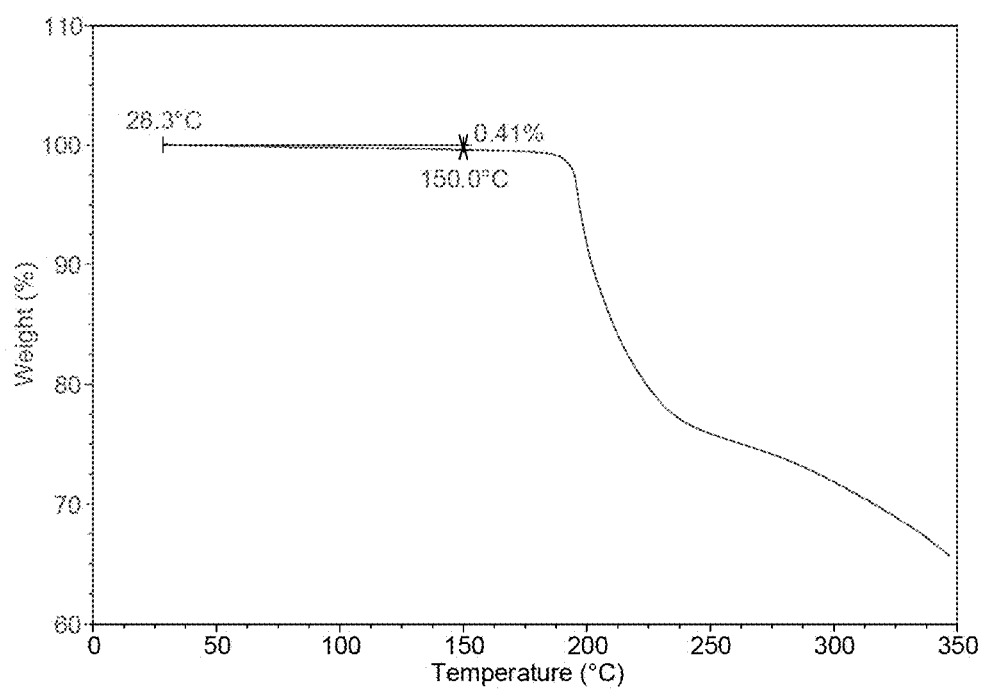
FIG. 5C is the thermogravimetric analysis pattern (TGA pattern) of crystal Form A of the maleate of the compound of Formula I in one embodiment of the present invention.
Figure 5D:
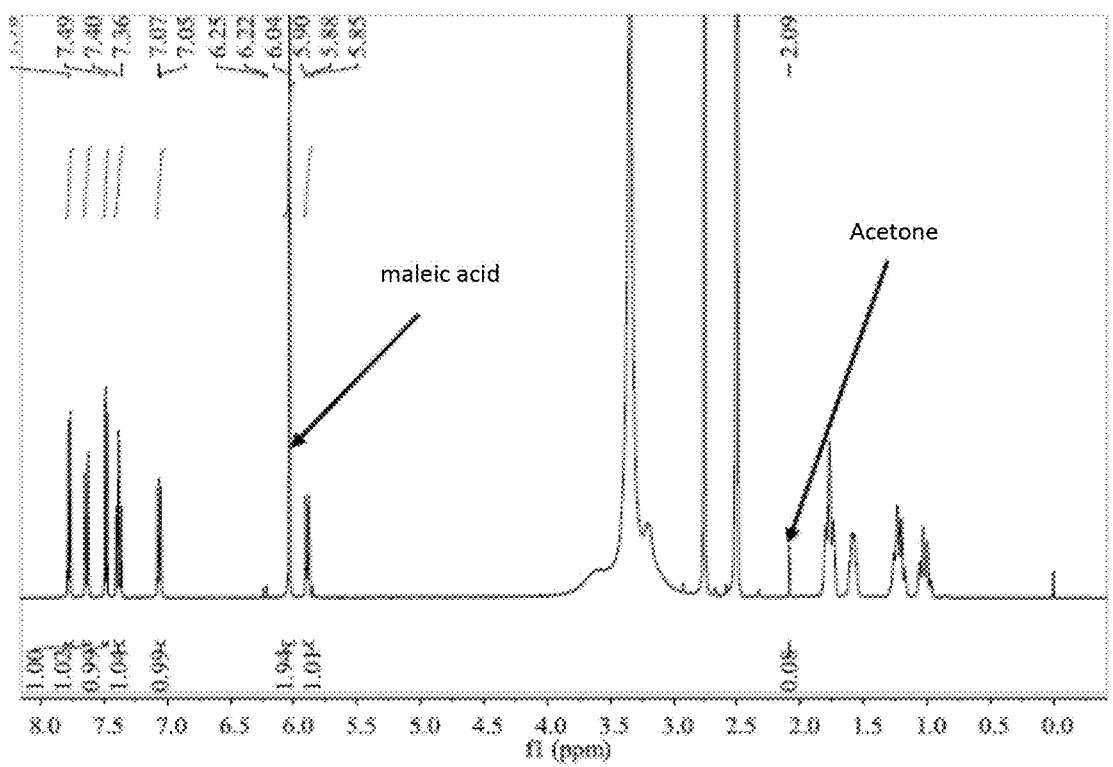
FIG. 5D is the $^1$H-NMR pattern of crystal Form A of the maleate of the compound of Formula I in one embodiment of the present invention.

For the maleate Form A of the compound of Formula I, the solubility in water is greater than 2.6 mg/ml; the DSC results of FIG. 5B show that the sample has one endothermic peak at 191.8° C.; TGA of FIG. 5C shows that the sample has a 0.41% weight loss when heated to 150° C. ¹H-NMR corresponds to 1:1 stoichiometry (free base:maleic acid), results are shown in FIG. 5D.

Preparation of maleate (b): 200 mg of the product from Example 1 was mixed and stirred with 1.05 molar ratio of maleic acid in isopropylamine (IPA) at room temperature for 5 days to obtain the maleate, which is in crystal form and is substantially the same as the X-ray diffraction pattern (XRPD), DSC pattern and TGA pattern of the above maleate Form A of the compound of Formula I.

Preparation of maleate (c): 200 mg of the product from Example 1 was mixed and stirred with 1.05 molar ratio of phosphoric acid in ethyl acetate (EtOAc) at room temperature for 5 days to obtain the maleate, which is in crystal form and is substantially the same as the X-ray diffraction pattern (XRPD), DSC pattern and TGA pattern of the above maleate Form A of the compound of Formula I.

Preparation of maleate (d): 200 mg of the product from Example 1 was mixed and stirred with 1.05 molar ratio of maleic acid in acetonitrile (ACN) at room temperature for 5 days to obtain the maleate, which is in crystal form and is substantially the same as the X-ray diffraction pattern (XRPD), DSC pattern and TGA pattern of the above maleate Form A of the compound of Formula I.

Preparation of maleate (e): 200 mg of the product from Example 1 was mixed and stirred with 1.05 molar ratio of maleic acid in methylbenzene (Toluene) at room temperature for 5 days to obtain, which is in crystal form and is substantially the same as the X-ray diffraction pattern (XRPD), DSC pattern and TGA pattern of the above maleate Form A of the compound of Formula I.

Comparative Example 1: Preparation and Identification of the Tartrate of N'-[trans-4-[2-[7-(benzo[b]thiophene)-7-piperazinyl]ethyl]cyclohexyl]-N,N-dimethylurea (Compound of Formula I)

Preparation of tartrate: 200 mg of the product from Example 1 was mixed and stirred with 1 molar ratio of tartaric acid in acetone at room temperature for 5 days. It is in crystal form, designated as tartrate Form A of the compound of Formula I.

Figure 6A:
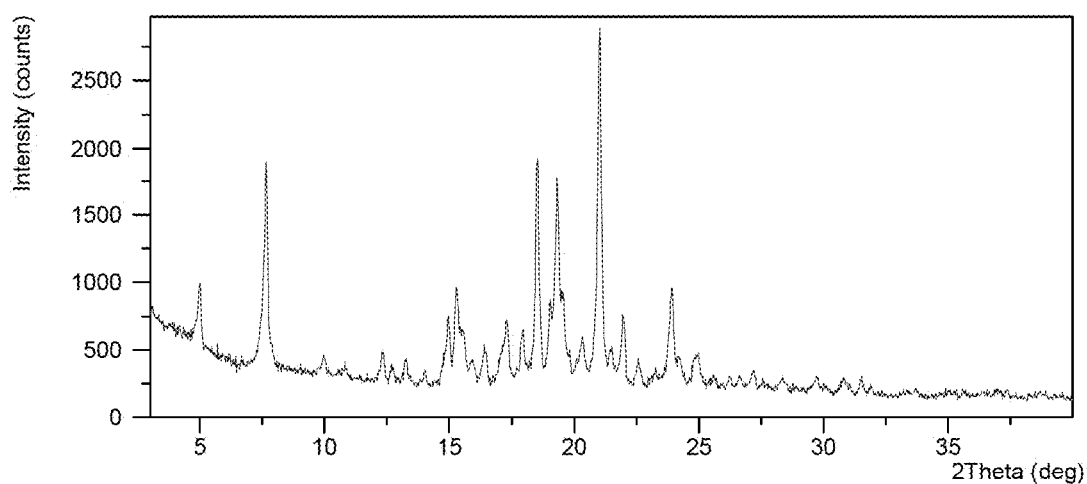
FIG. 6A is the X-ray powder diffraction pattern (XPRD pattern) of the tartrate of the compound of Formula I in one embodiment of the present invention.
Figure 6B:
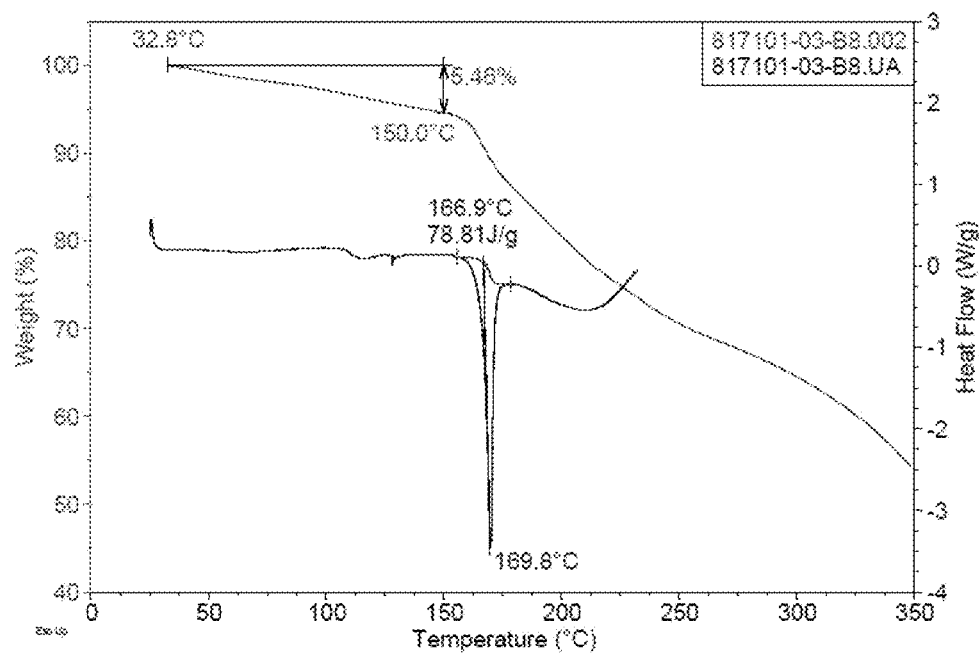
FIG. 6B is the differential scanning calorimetry pattern (DSC pattern) of the tartrate of the compound of Formula I in one embodiment of the present invention. The abscissa is temperature (° C.); the ordinate is the heat flux (W/g) and thermogravimetric analysis pattern (TGA pattern).

With respect to tartrate Form A of the compound of Formula I, FIG. 6A shows a powder X-ray diffraction pattern (XRPD); the DSC results of FIG. 6B show that the sample has one endothermic peak at 169.8° C.; TGA of FIG. 6B shows a 5.5% weight loss of the sample when heated to 150° C. ¹H-NMR corresponds to 1:1 stoichiometry (free base: tartaric acid).

Comparative Example 2: Preparation and Identification of the Fumarate of N'-[trans-4-[2-[7-(benzo[b]thiophene)-7-piperazinyl]ethyl]cyclohexyl]-N,N-dimethylurea (Compound of Formula I)

Preparation of fumarate: 200 mg of the product from Example 1 was mixed and stirred with 1 molar ratio of fumaric acid in acetone at room temperature for 5 days. It is in crystal form, designated as fumarate Form A of the compound of Formula I.

Figure 7A:
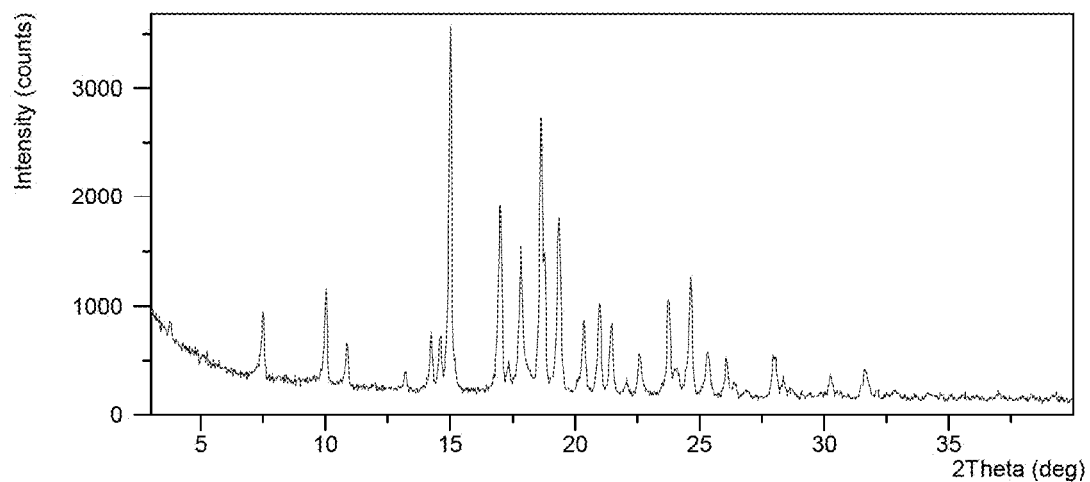
FIG. 7A is the X-ray powder diffraction pattern (XPRD pattern) of the fumarate of the compound of Formula I in one embodiment of the present invention.
Figure 7B:
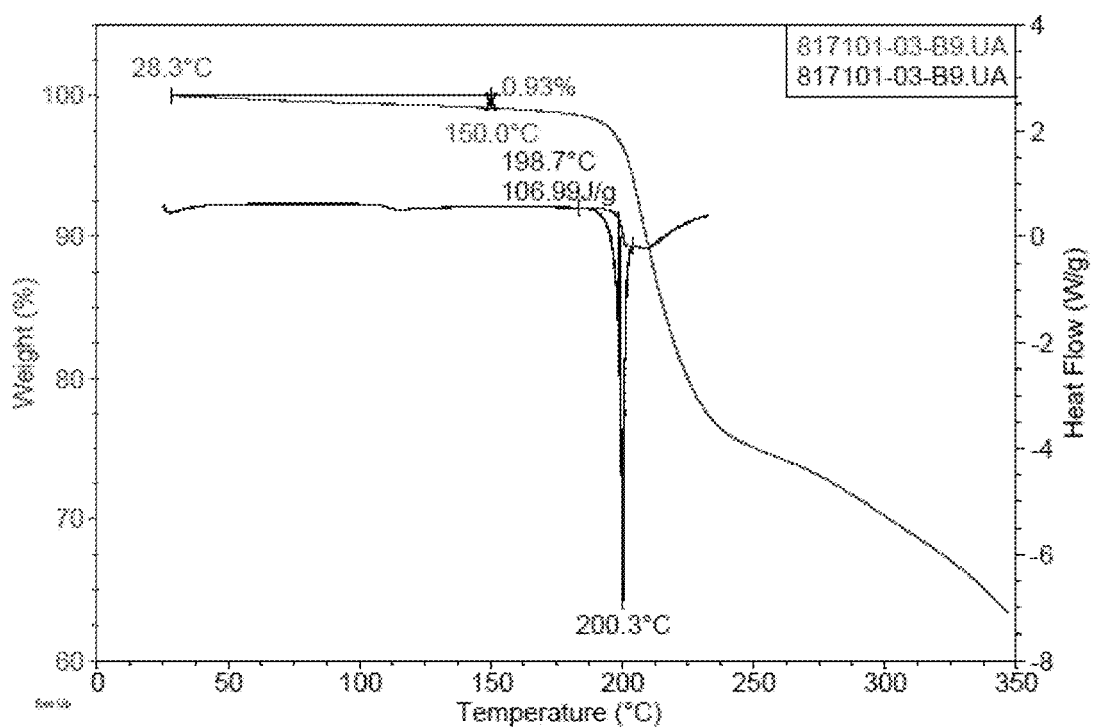
FIG. 7B is the differential scanning calorimetry pattern (DSC pattern) of the fumarate of the compound of Formula I in one embodiment of the present invention. The abscissa is temperature (° C.); the ordinate is the heat flux (W/g) and thermogravimetric analysis pattern (TGA pattern).

With respect to fumarate Form A of the compound of Formula I, FIG. 7A shows a powder X-ray diffraction pattern (XRPD); the DSC results of FIG. 7B show that the sample has one endothermic peak at 200.3° C.; TGA of FIG. 7B shows a 0.9% weight loss of the sample when heated to 150° C. ¹H-NMR corresponds to 1:1 stoichiometry (free base: fumaric acid).

Comparative Example 3: Preparation and Identification of the Citrate of N'-[trans-4-[2-[7-(benzo[b]thiophene)-7-piperazinyl]ethyl]cyclohexyl]-N,N-dimethylurea (Compound of Formula I)

Preparation of citrate: 200 mg of the product from Example 1 was mixed and stirred with 1 molar ratio of citric acid in ethyl acetate (EtOAc) at room temperature for 5 days. It is in crystal form, designated as citrate Form A of the compound of Formula I.

Figure 8A:
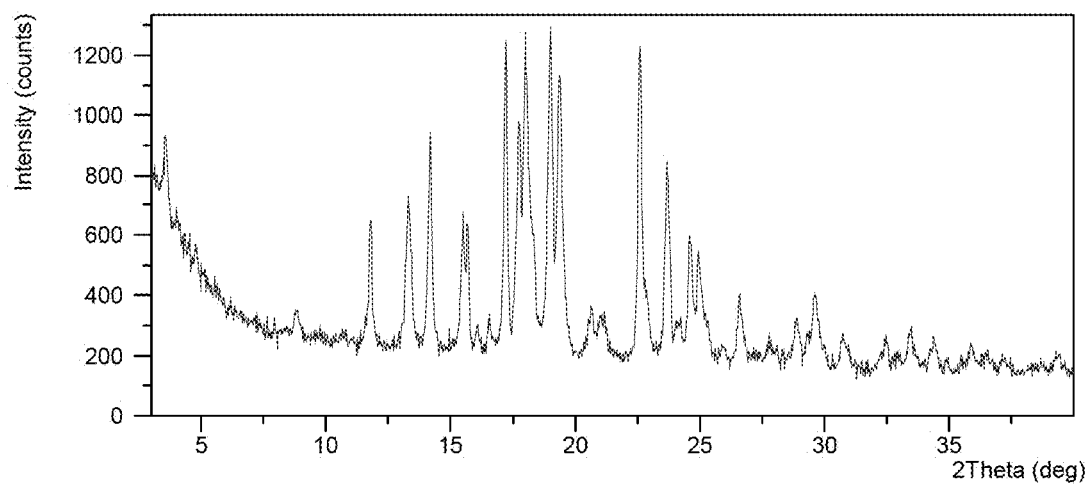
FIG. 8A is the X-ray powder diffraction pattern (XPRD pattern) of the citrate of the compound of Formula I in one embodiment of the present invention.
Figure 8B:
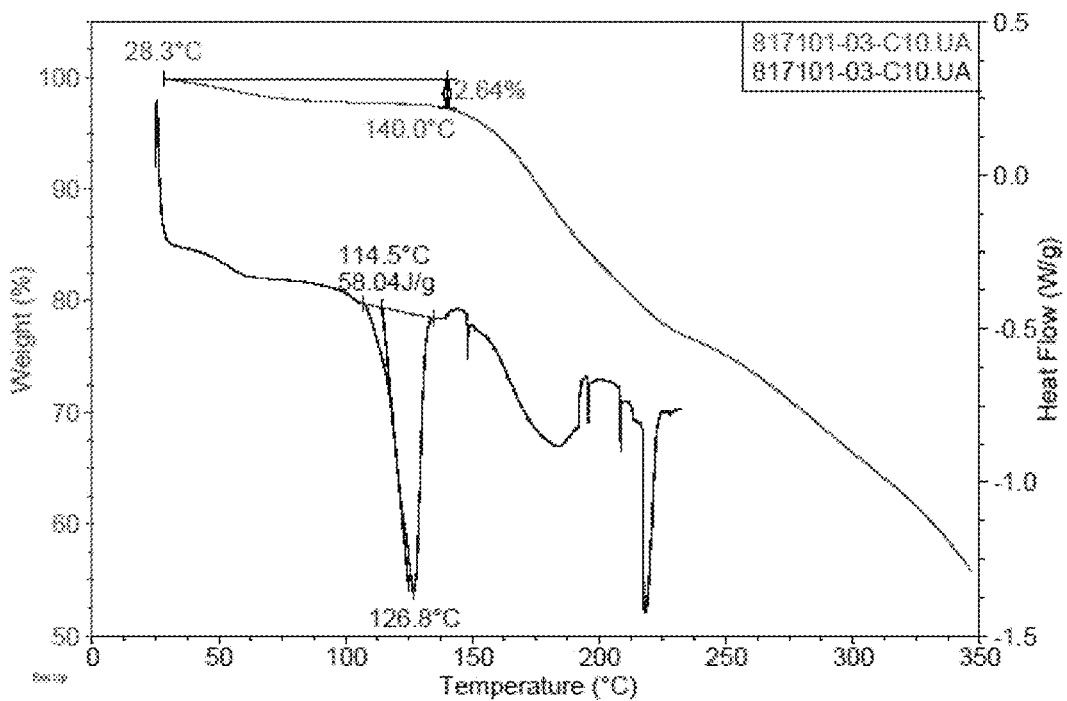
FIG. 8B is the differential scanning calorimetry pattern (DSC pattern) of the citrate of the compound of Formula I in one embodiment of the present invention. The abscissa is temperature (° C.); the ordinate is the heat flux (W/g) and thermogravimetric analysis pattern (TGA pattern).

With respect to citrate Form A of the compound of Formula I, FIG. 8A shows a powder X-ray diffraction pattern (XRPD); the DSC results of FIG. 8B show that the sample has one endothermic peak at 126.8° C.; TGA of FIG. 8B shows a 2.6% weight loss of the sample when heated to 140° C. ¹H-NMR corresponds to 1:1 stoichiometry (free base: citric acid).

Comparative Example 4: Preparation and Identification of the Glycolate of N'-[trans-4-[2-[7-(benzo[b]thiophene)-7-piperazinyl]ethyl]cyclohexyl]-N,N-dimethylurea (Compound of Formula I)

Preparation of glycolate: 200 mg of the product from Example 1 was mixed and stirred with 1 molar ratio of glycollic acid in isopropylamine (IPA) at room temperature for 5 days. It is in crystal form, designated as glycolate Form A of the compound of Formula I.

Figure 9A:
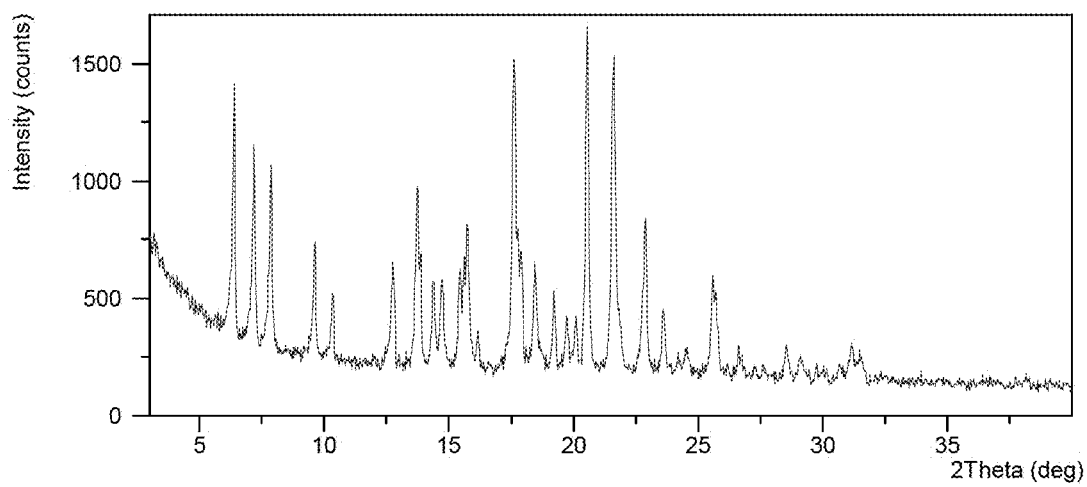
FIG. 9A is the X-ray powder diffraction pattern (XPRD pattern) of the glycolate of the compound of Formula I in one embodiment of the present invention.
Figure 9B:
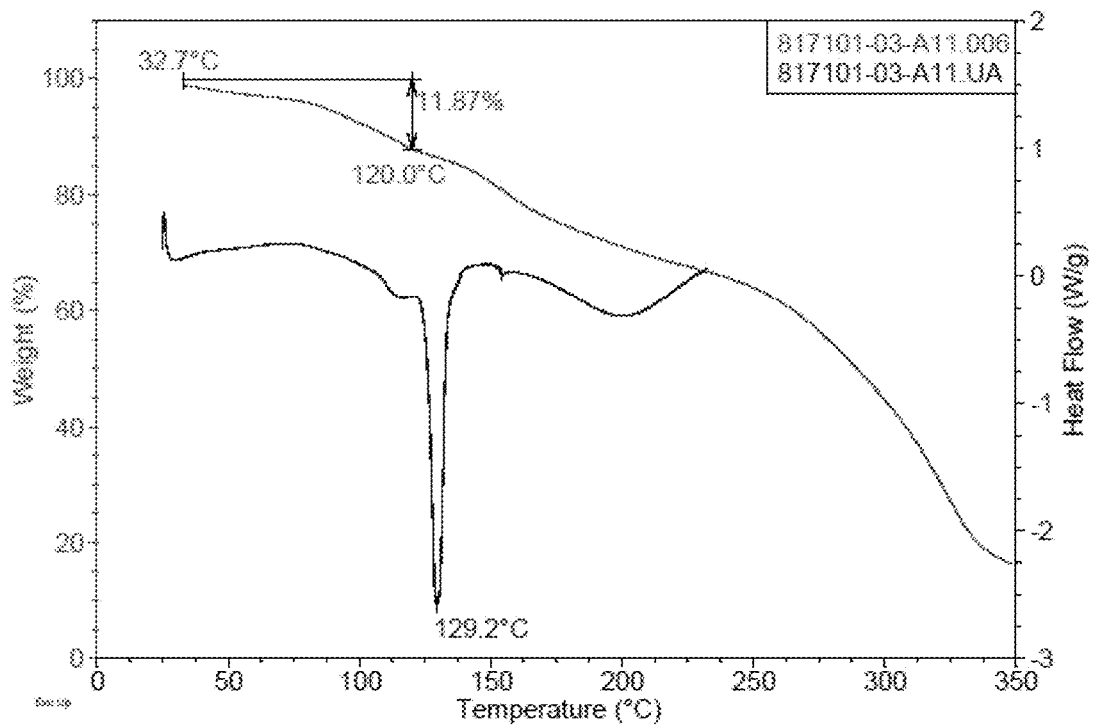
FIG. 9B is the differential scanning calorimetry pattern (DSC pattern) of the glycolate of the compound of Formula I in one embodiment of the present invention. The abscissa is temperature (° C.); the ordinate is the heat flux (W/g) and thermogravimetric analysis pattern (TGA pattern).

With respect to glycolate Form A of the compound of Formula I, FIG. 9A shows a powder X-ray diffraction pattern (XRPD); the DSC results of FIG. 9B show that the sample has one endothermic peak at 129.2° C.; TGA of FIG. 9B shows a 11.9% weight loss of the sample when heated to 120° C. $^1$H-NMR corresponds to 1:1 stoichiometry (free base:glycollic acid).

Comparative Example 5: Preparation and Identification of the Malate of N'-[trans-4-[2-[7-(benzo[b]thiophene)-7-piperazinyl]ethyl]cyclohexyl]-N,N-dimethylurea (Compound of Formula I)

Preparation of malate: 200 mg of the product from Example 1 was mixed and stirred with 1 molar ratio of L-malic acid in Acetone at room temperature for 5 days. It is in crystal form, designated as malate Form A of the compound of Formula I.

Figure 10A:
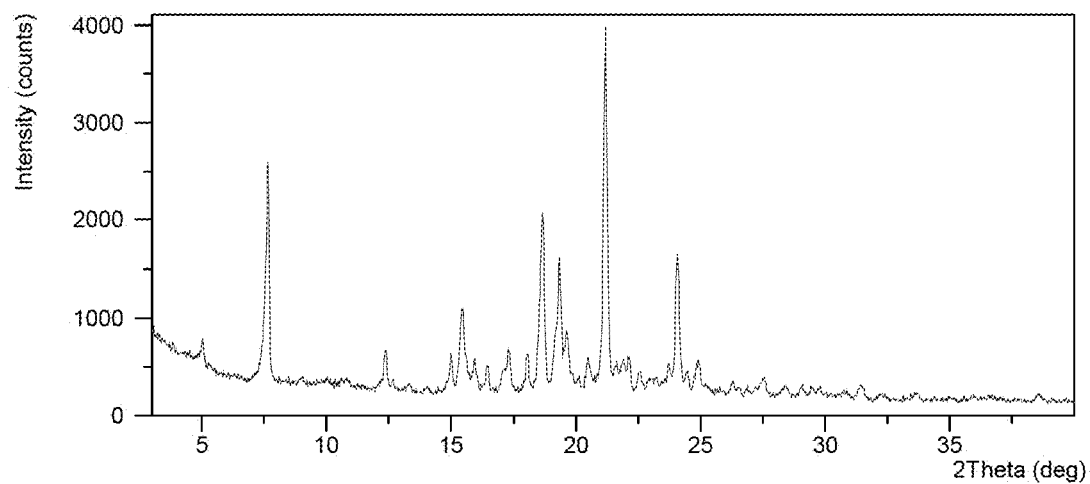
FIG. 10A is the X-ray powder diffraction pattern (XPRD pattern) of the malate of the compound of Formula I in one embodiment of the present invention.
Figure 10B:
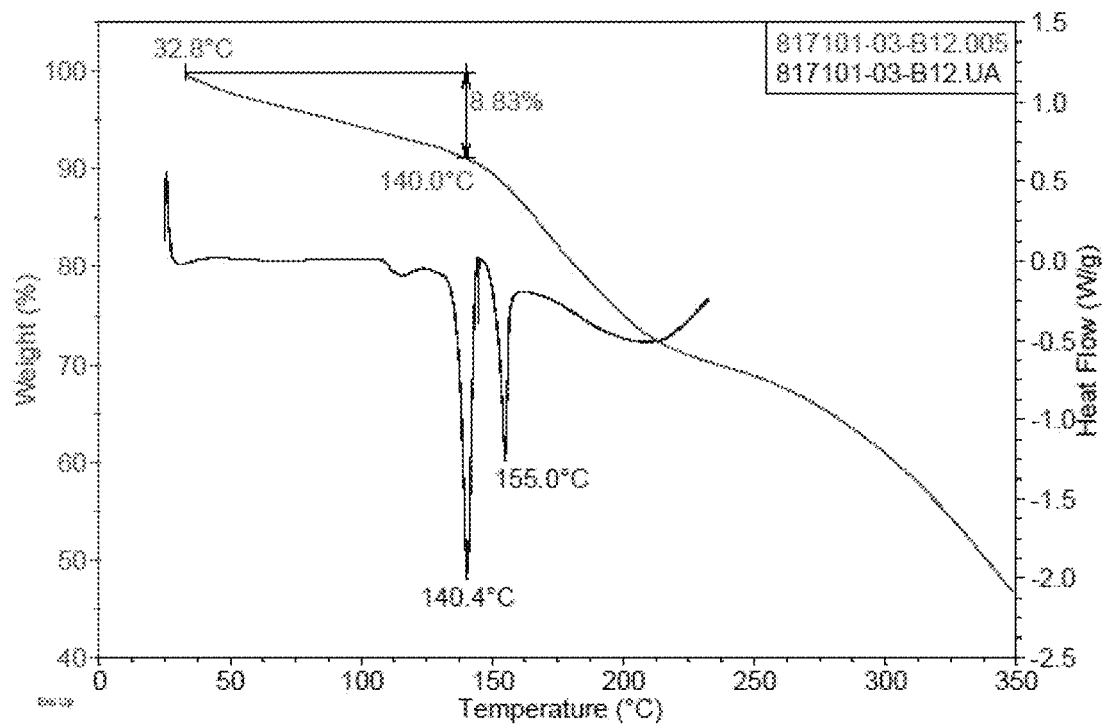
FIG. 10B is the differential scanning calorimetry pattern (DSC pattern) of the malate of the compound of Formula I in one embodiment of the present invention. The abscissa is temperature (° C.); the ordinate is the heat flux (W/g) and thermogravimetric analysis pattern (TGA pattern).

With respect to malate Form A of the compound of Formula I, FIG. 10A shows a powder X-ray diffraction pattern (XRPD); The DSC results of FIG. 10B show that the sample has two endothermic peaks at 140.4 and 155.0° C.; TGA of FIG. 10B shows a 8.8% weight loss of the sample when heated to 140° C. $^1$H-NMR corresponds to 1:1 stoichiometry (free base:malic acid).

Comparative Example 6: Preparation and Identification of the DL-Lactate of N'-[trans-4-[2-[7-(benzo[b]thiophene)-7-piperazinyl]ethyl]cyclohexyl]-N,N-dimethylurea (Compound of Formula I)

Preparation of lactate: 200 mg of the product from Example 1 was mixed and stirred with 1 molar ratio of DL-lactic acid in ethyl acetate (EtOAc) at room temperature for 5 days. It is in crystal form, designated as lactate Form A of the compound of Formula I.

Figure 11A:
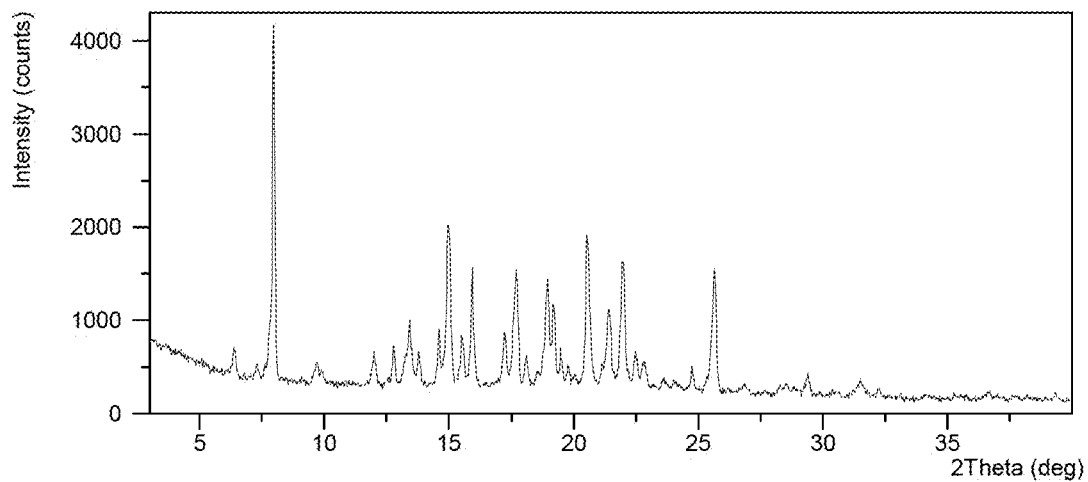
FIG. 11A is the X-ray powder diffraction pattern (XPRD pattern) of the lactate of the compound of Formula I in one embodiment of the present invention.
Figure 11B:
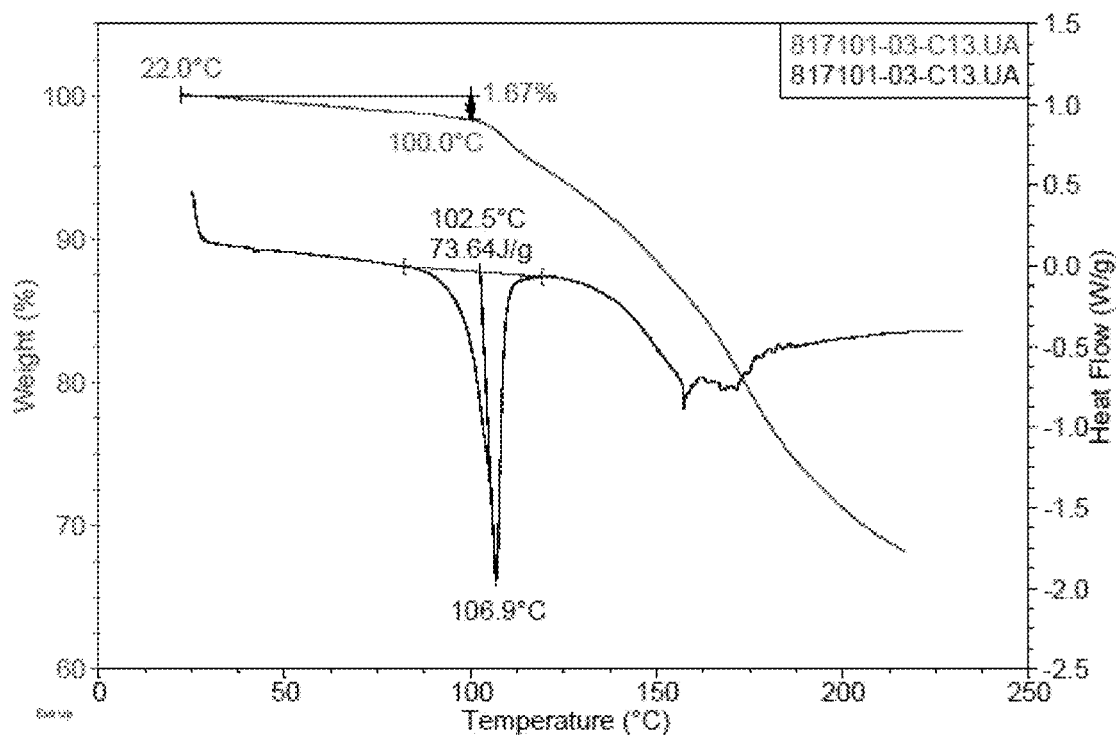
FIG. 11B is the differential scanning calorimetry pattern (DSC pattern) of the lactate of the compound of Formula I in one embodiment of the present invention. The abscissa is temperature (° C.); the ordinate is the heat flux (W/g) and thermogravimetric analysis pattern (TGA pattern).

With respect to lactate Form A of the compound of Formula I, FIG. 11A shows a powder X-ray diffraction pattern (XRPD); the DSC results of FIG. 11B show that the sample has one endothermic peak at 106.9° C.; TGA of FIG. 11B shows a 1.7% weight loss of the sample when heated to 100° C. $^1$H-NMR corresponds to 1:1 stoichiometry (free base:lactic acid).

Comparative Example 7: Preparation and Identification of the Succinate of N'-[trans-4-[2-[7-(benzo[b]thiophene)-7-piperazinyl]ethyl]cyclohexyl]-N,N-dimethylurea (Compound of Formula I)

Preparation of succinate: 200 mg of the product from Example 1 was mixed and stirred with 1 molar ratio of succinic acid in ethyl acetate (EtOAc) at room temperature for 5 days. It is in crystal form, designated as succinate Form A of the compound of Formula I.

Figure 12A:
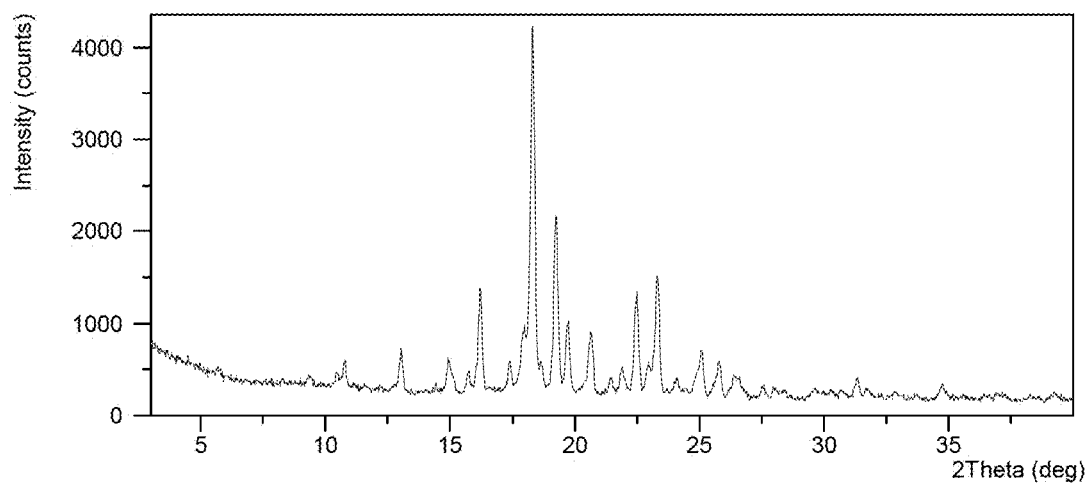
FIG. 12A is the X-ray powder diffraction pattern (XPRD pattern) of the succinate of the compound of Formula I in one embodiment of the present invention.
Figure 12B:
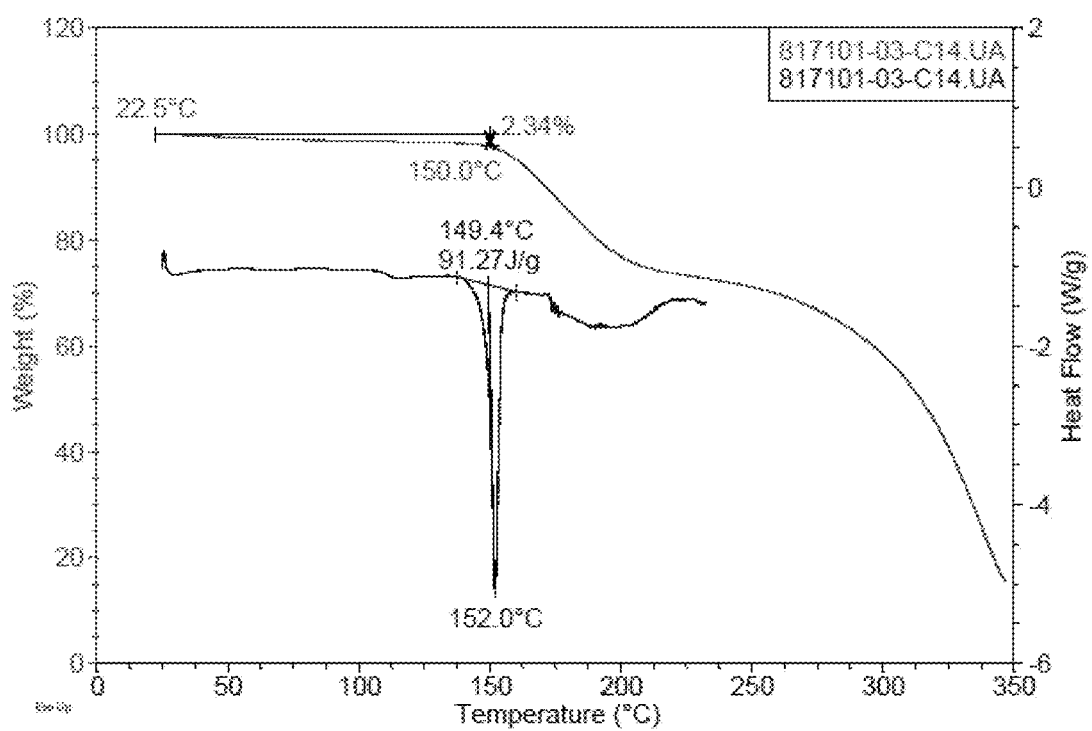
FIG. 12B is the differential scanning calorimetry pattern (DSC pattern) of the succinate of the compound of Formula I in one embodiment of the present invention. The abscissa is temperature (° C.); the ordinate is the heat flux (W/g) and thermogravimetric analysis pattern (TGA pattern).

With respect to succinate Form A of the compound of Formula I, FIG. 12A shows a powder X-ray diffraction pattern (XRPD); the DSC results of FIG. 12B show that the sample has one endothermic peak at 152.0° C.; TGA of FIG. 12B shows a 2.3% weight loss of the sample when heated to 150° C. $^1$H-NMR corresponds to 1:1 stoichiometry (free base:succinic acid).

Comparative Example 8: Preparation and Identification of the Adipate of N'-[trans-4-[2-[7-(benzo[b]thiophene)-7-piperazinyl]ethyl]cyclohexyl]-N,N-dimethylurea (Compound of Formula I)

Preparation of adipate: 200 mg of the product from Example 1 was mixed and stirred with 1 molar ratio of adipic acid in ethyl acetate (EtOAc) at room temperature for 5 days. It is in crystal form, designated as adipate Form A of the compound of Formula I.

Figure 13A:
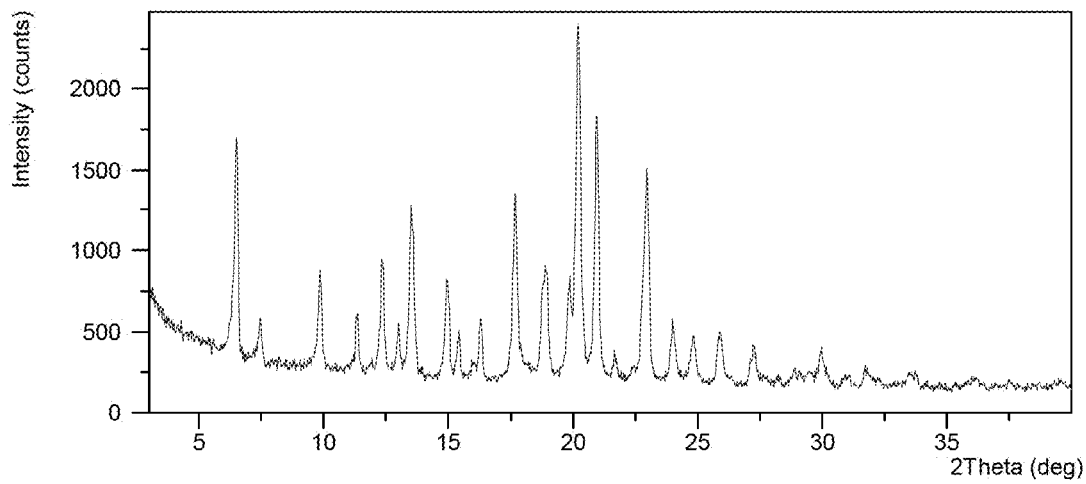
FIG. 13A is the X-ray powder diffraction pattern (XPRD pattern) of the adipate of the compound of Formula I in one embodiment of the present invention.
Figure 13B:
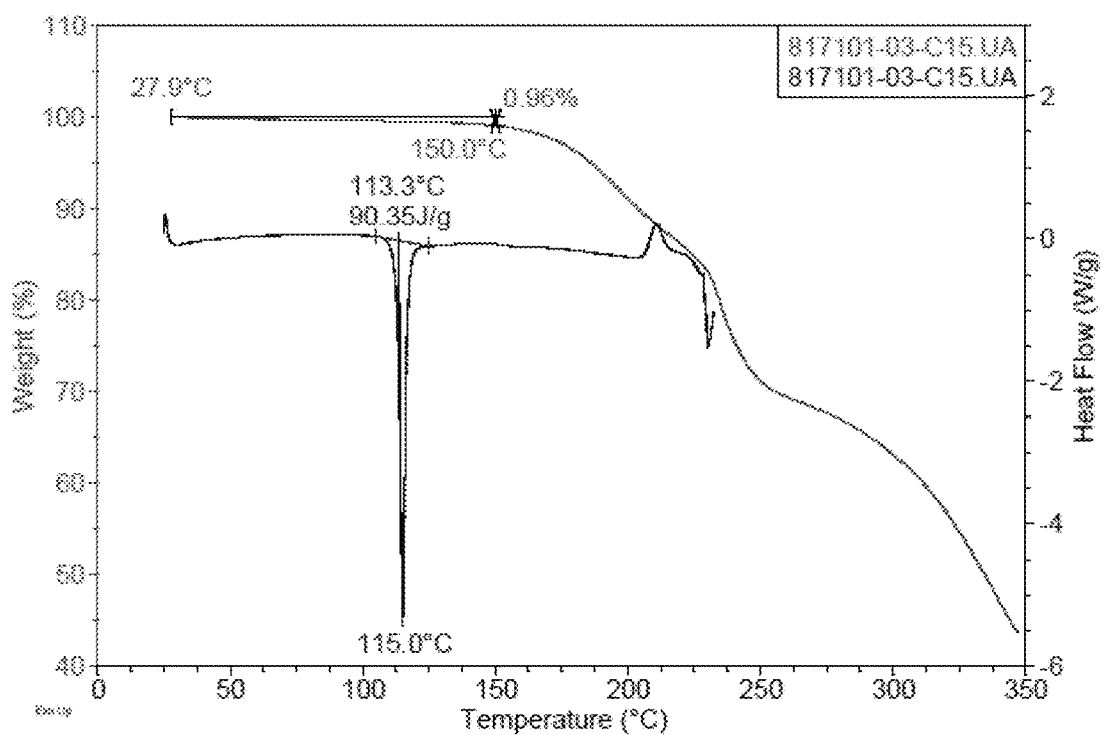
FIG. 13B is the differential scanning calorimetry pattern (DSC pattern) of the adipate of the compound of Formula I in one embodiment of the present invention. The abscissa is temperature (° C.); the ordinate is the heat flux (W/g) and thermogravimetric analysis pattern (TGA pattern).

With respect to adipate Form A of the compound of Formula I, FIG. 13A shows a powder X-ray diffraction pattern (XRPD), TGA of FIG. 13B shows a 1.0% weight loss of the sample when heated to 150° C.; the DSC results of FIG. 13B show that the sample has one endothermic peak at 115.0° C. $^1$H-NMR corresponds to 1:1 stoichiometry (free base:adipic acid).

Comparative Example 9: Preparation and Identification of the p-Toluenesulfonate of N'-[trans-4-[2-[7-(benzo[b]thiophene)-7-piperazinyl]ethyl]cyclohexyl]-N,N-dimethylurea (Compound of Formula I)

Preparation of p-toluenesulfonate: 200 mg of the product from Example 1 was mixed and stirred with 1 molar ratio of p-toluenesulfonic acid in ethyl acetate (EtOAc) at room temperature for 5 days. It is in crystal form, designated as p-toluenesulfonate Form A of the compound of Formula I.

Figure 14A:
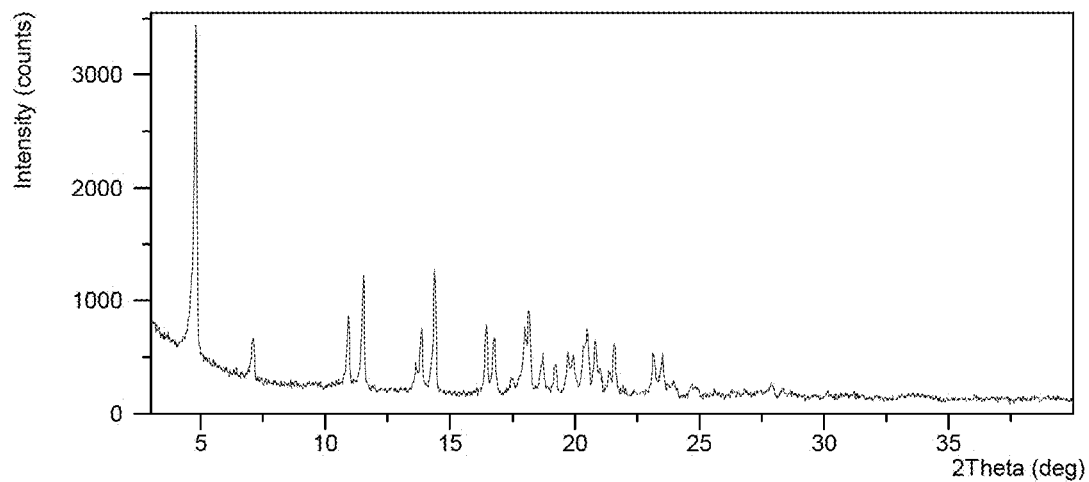
FIG. 14A is the X-ray powder diffraction pattern (XPRD pattern) of the p-toluenesulfonate of the compound of Formula I in one embodiment of the present invention.
Figure 14B:
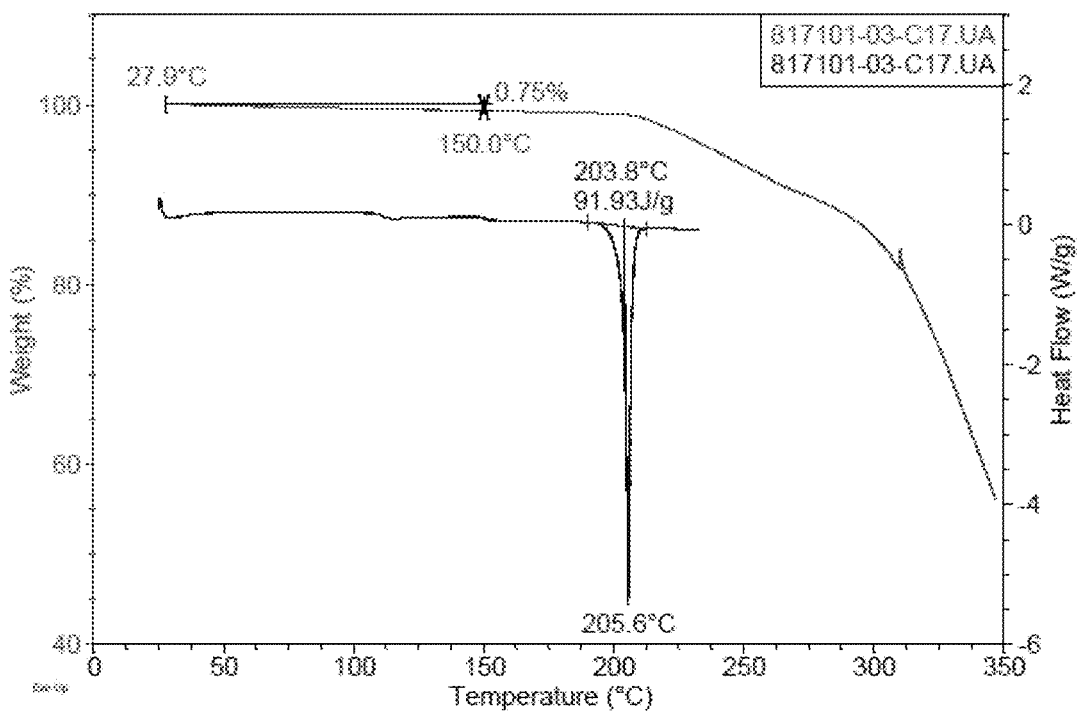
FIG. 14B is the differential scanning calorimetry pattern (DSC pattern) of the p-toluenesulfonate of the compound of Formula I in one embodiment of the present invention. The abscissa is temperature (° C.); the ordinate is the heat flux (W/g) and thermogravimetric analysis pattern (TGA pattern).

With respect to p-toluenesulfonate Form A of the compound of Formula I, FIG. 14A shows a powder X-ray diffraction pattern (XRPD); the DSC results of FIG. 14B show that the sample has one endothermic peak at 205.6° C.; TGA of FIG. 14B shows that the sample had a 0.8% weight loss when heated to 150° C. $^1$H-NMR corresponds to 1:1 stoichiometry (free base:p-toluenesulfonic acid).

Comparative Example 10: Preparation and Identification of the Mesylate of N'-[trans-4-[2-[7-(benzo[b]thiophene)-7-piperazinyl]ethyl]cyclohexyl]-N,N-dimethylurea (Compound of Formula I)

Preparation of mesylate: 200 mg of the product from Example 1 were stirred with 1 molar ratio of methylsulfonic acid in isopropylamine (IPA) at room temperature for 5 days. It is in crystal form, designated as mesylate Form A of the compound of Formula I.

Figure 15A:
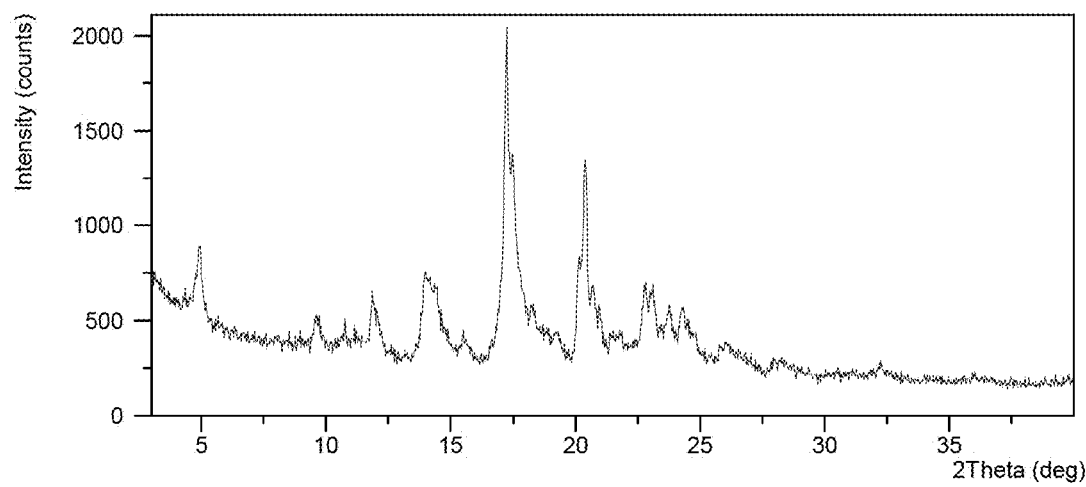
FIG. 15A is the X-ray powder diffraction pattern (XPRD pattern) of the mesylate of the compound of Formula I in one embodiment of the present invention.
Figure 15B:
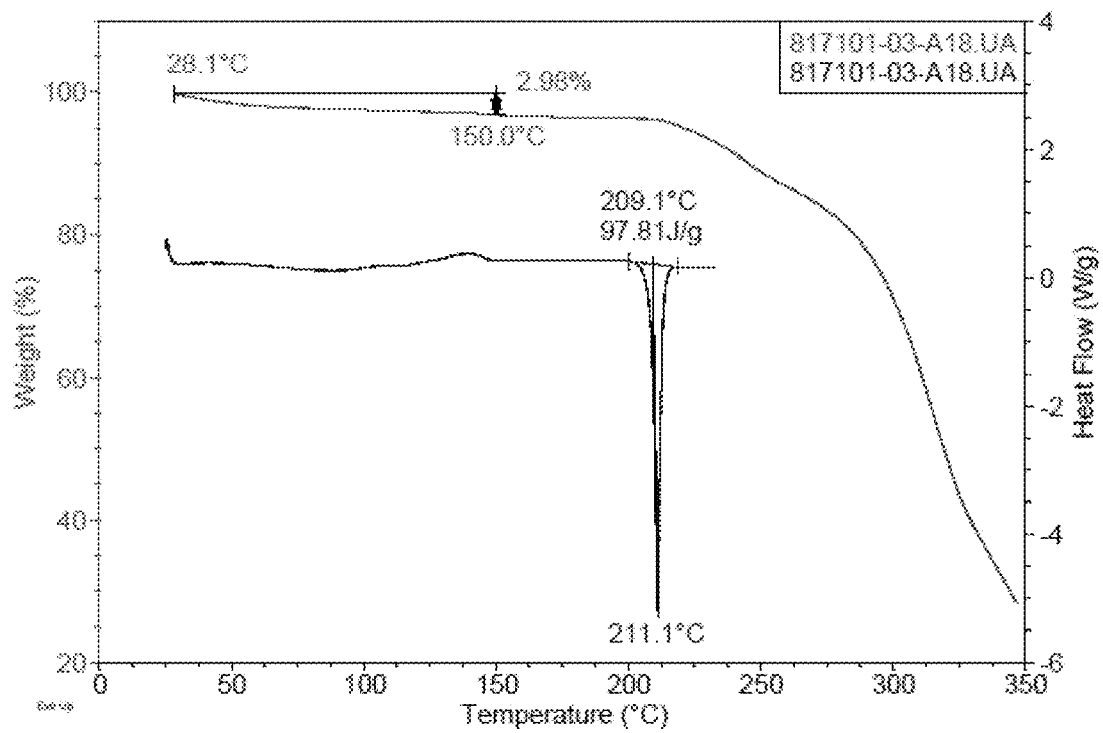
FIG. 15B is the differential scanning calorimetry pattern (DSC pattern) of the mesylate of the compound of Formula I in one embodiment of the present invention. The abscissa is temperature (° C.); the ordinate is the heat flux (W/g) and thermogravimetric analysis pattern (TGA pattern).

With respect to mesylate Form A of the compound of Formula I, FIG. 15A shows a powder X-ray diffraction pattern (XRPD); the DSC results of FIG. 15B show that the sample has one endothermic peak at 211.1° C.; TGA of FIG. 15B shows a 3.0% weight loss of the sample when heated to 150° C. $^1$H-NMR corresponds to 1:1 stoichiometry (free base:methylsulfonic acid).

Comparative Example 11: Preparation and Identification of Crystalline Form a of Hydrobromide Salt of N'-[trans-4-[2-[7-(benzo[b]thiophene)-7-piperazinyl]ethyl]cyclohexyl]-N,N-dimethylurea (Compound of Formula I)

Preparation of hydrobromide salt: 200 mg of the product from Example 1 was mixed and stirred with 1 molar ratio of hydrobromic acid in ethyl acetate (EtOAc) at room temperature for 5 days. It is in crystal form, designated as hydrobromide salt Form A of the compound of Formula I.

Figure 16A:
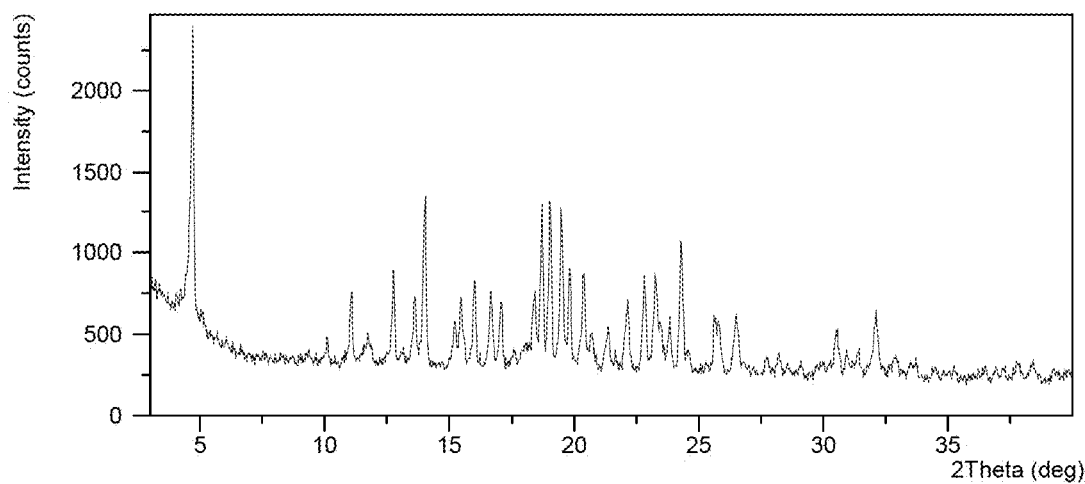
FIG. 16A is the X-ray powder diffraction pattern (XPRD pattern) of the hydrobromide salt of the compound of Formula I in one embodiment of the present invention.
Figure 16B:
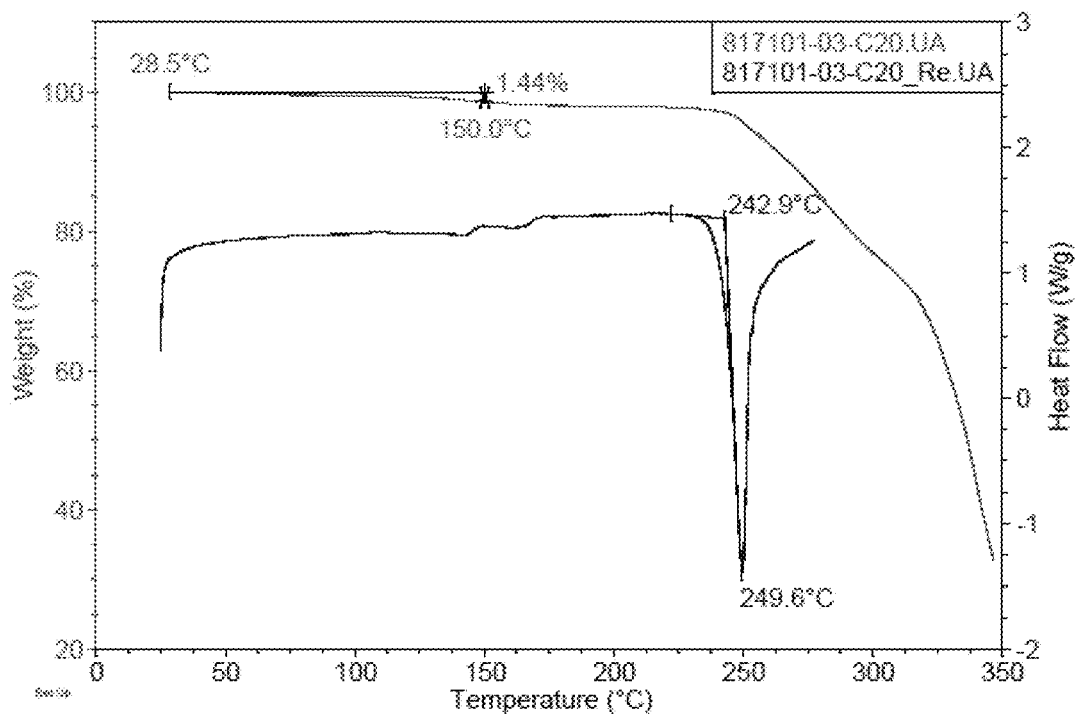
FIG. 16B is the differential scanning calorimetry pattern (DSC pattern) of the hydrobromide salt of the compound of Formula I in one embodiment of the present invention. The abscissa is temperature (° C.); the ordinate is the heat flux (W/g) and thermogravimetric analysis pattern (TGA pattern).

With respect to hydrobromide salt Form A of the compound of Formula I, FIG. 16A shows a powder X-ray diffraction pattern (XRPD); the DSC results of FIG. 16B show that the sample has one endothermic peak at 249.6° C.; TGA of FIG. 16B shows a 1.4% weight loss of the sample when heated to 150° C. $^1$H-NMR corresponds to 1:1 stoichiometry (free base:hydrobromic acid).

Through analysis of the XRPD pattern, DSC pattern and TGA pattern of the above salts and crystal forms, based on the higher degree of crystallinity, less TGA weight loss, higher and unique DSC endothermic signal combined with the acid safety level, it can be concluded that the hydrochloride salt, sulfate, phosphate and maleate of the compounds of Formula I are preferred.

Comparative Example 12: Preparation and Identification of the Maleate of N'-[trans-4-[2-[7-(benzo[b]thiophene)-7-piperazinyl]ethyl]cyclohexyl]-N,N-dimethylurea (Compound of Formula I)

Preparation of maleate: the maleate was obtained by adding an anti-solvent to 200 mg of the product from Example 1 in a $CHCl_3$/IPAc (chloroform/isopropyl acetate) system. It is in crystal form, designated as maleate Form B of the compound of Formula I.

Figure 17A:
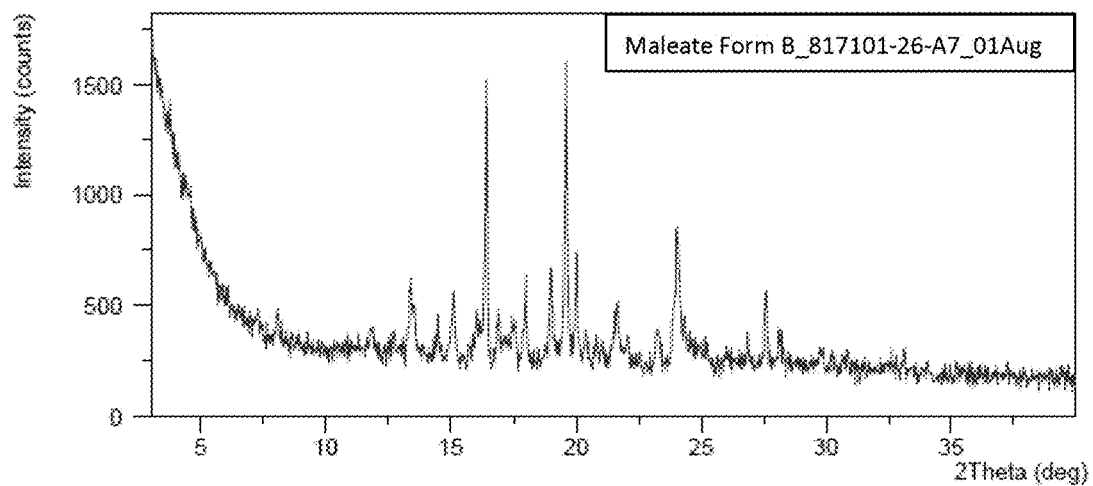
FIG. 17A is the X-ray powder diffraction pattern (XPRD pattern) of crystal Form B of the maleate of the compound of Formula I in one embodiment of the present invention.

FIG. 17A shows a powder X-ray diffraction pattern (XRPD).

Figure 17B:
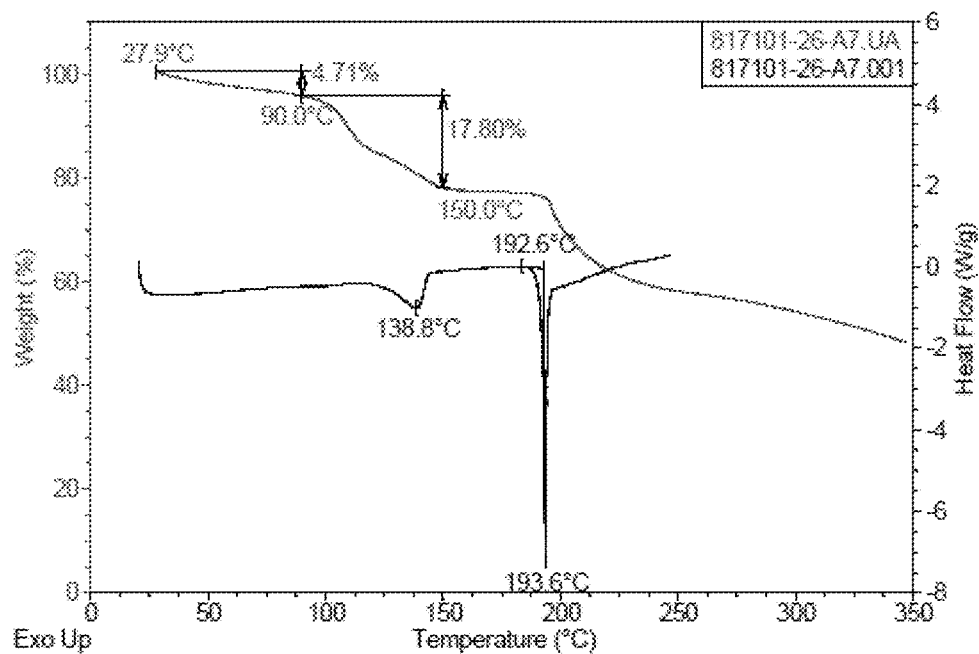
FIG. 17B is the differential scanning calorimetry pattern (DSC pattern) of crystal Form B of the maleate of the compound of Formula I in one embodiment of the present invention. The abscissa is temperature (° C.); the ordinate is the heat flux (W/g) and thermogravimetric analysis pattern (TGA pattern).
Figure 17C:
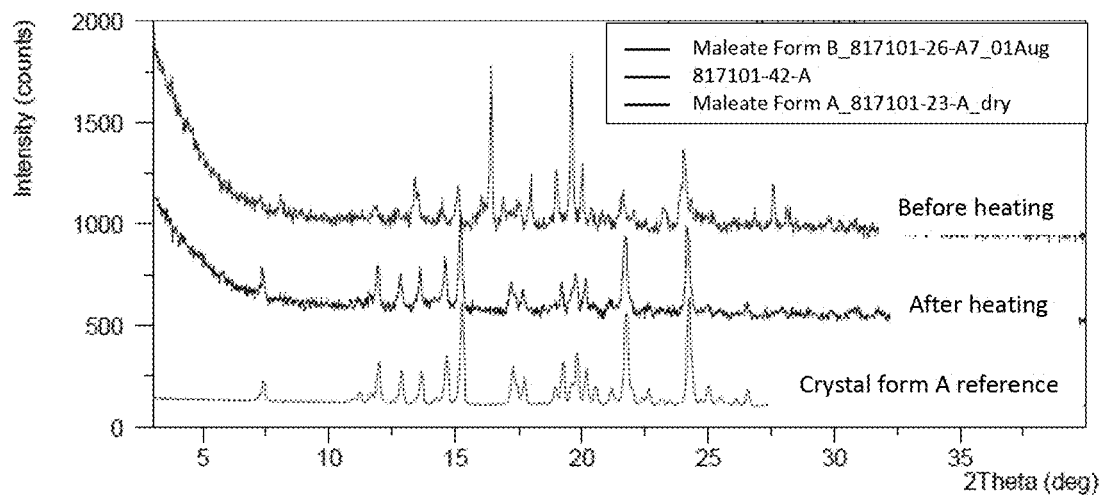
FIG. 17C is the XRPD pattern of crystal Form B of the maleate of the compound of Formula I in one embodiment of the present invention before and after heating.
Figure 18A:
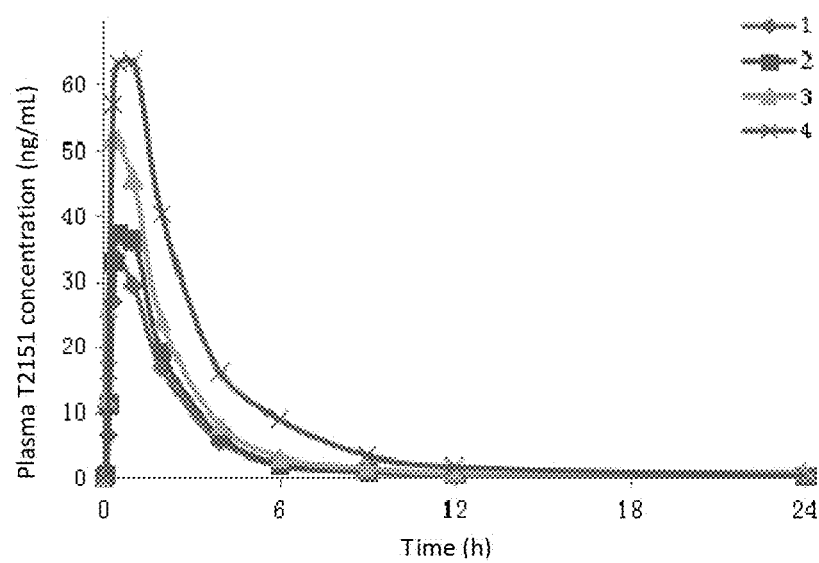
FIG. 18A is the graph of individual plasma concentration versus time after intragastric administration of 1 mg/kg of the compound of Formula I to rats.
Figure 18B:
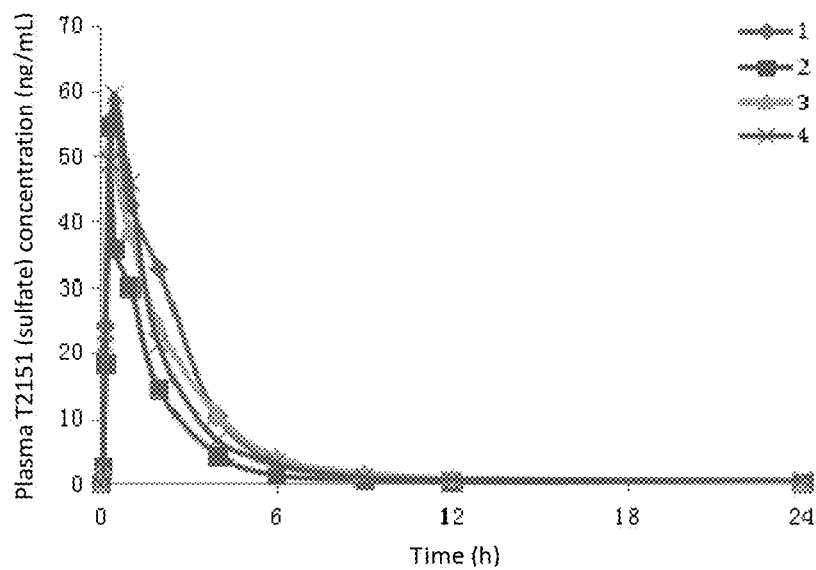
FIG. 18B is the graph of individual plasma concentration versus time after intragastric administration of 1 mg/kg of the sulfate of the compound of Formula I to rats.
Figure 18C:
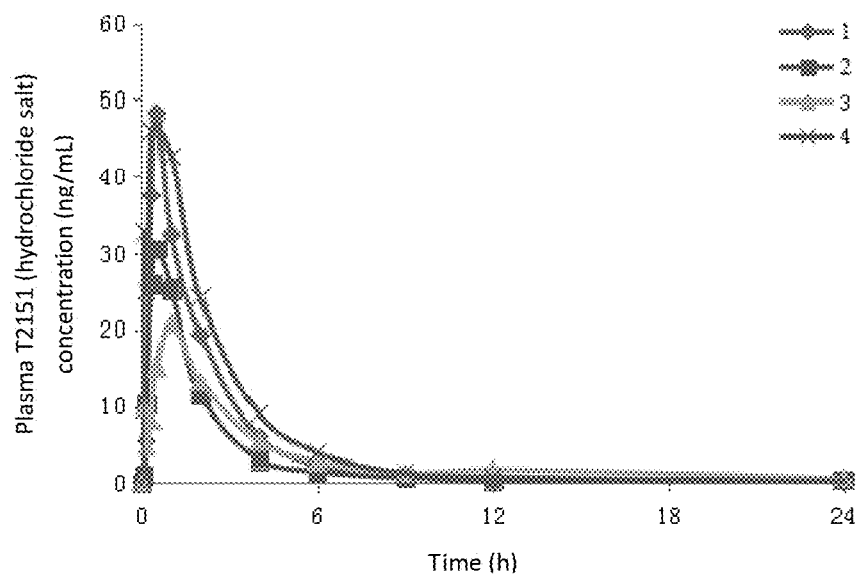
FIG. 18C is the graph of individual plasma concentration versus time after intragastric administration of 1 mg/kg of the hydrochloride salt of the compound of Formula I to rats.
Figure 18D:
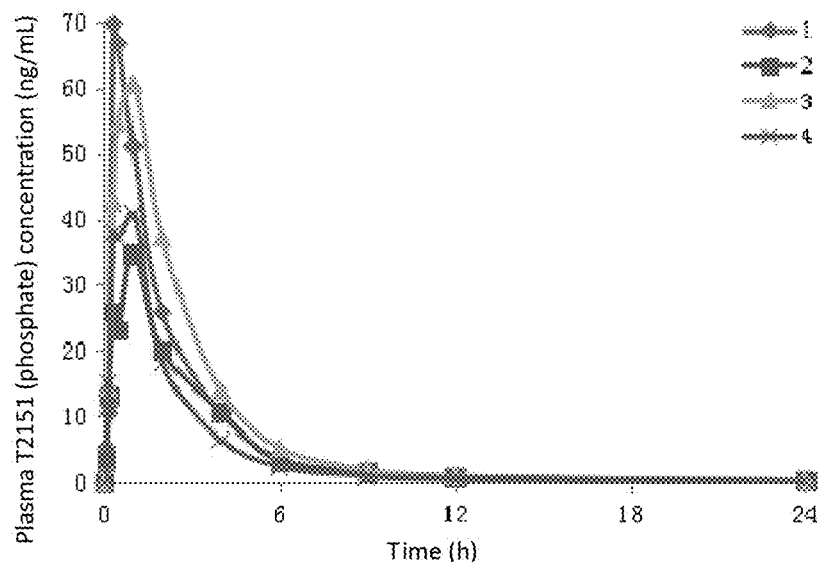
FIG. 18D is the graph of individual plasma concentration versus time after intragastric administration of 1 mg/kg of the phosphate of the compound of Formula I to rats.
Figure 18E:
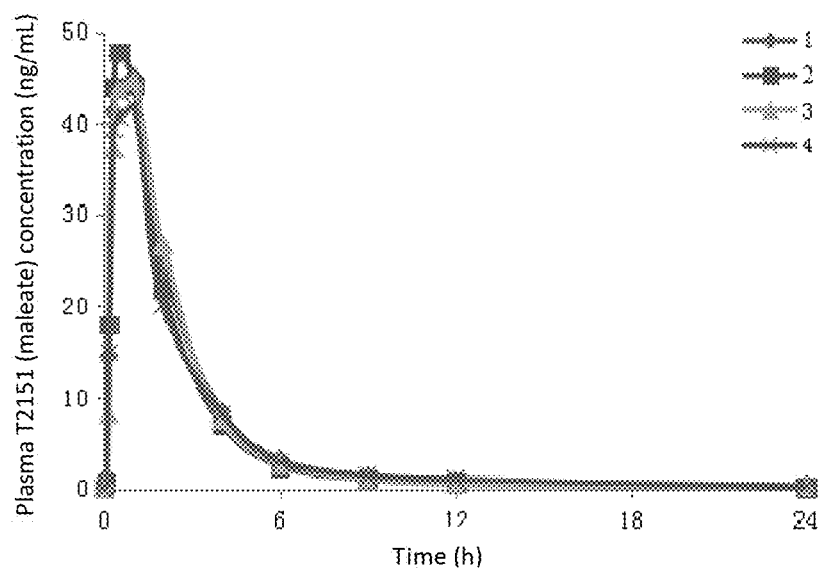
FIG. 18E is the graph of individual plasma concentration versus time after intragastric administration of 1 mg/kg of the maleate of the compound of Formula I to rats.

With respect to maleate Form B of the compound of Formula I, it shows a powder X-ray diffraction pattern (XRPD); the DSC results of FIG. 17B show that the sample has two endothermic peaks at 138.8° C. and 193.6° C.; TGA of FIG. 17B shows a 4.7% weight loss of the sample when heated to 90° C. and a 17.8% weight loss of the sample when continued heating to 150° C. $^1$H-NMR corresponds to 1:1 stoichiometry (free base:maleic acid); and after maleate Form B was heated to 150° C. and cooled to room temperature, it turned to maleate Form A, and the results are shown in FIG. 17C.

Compared with maleate Form A, maleate Form B can be turned to maleate Form A after being heated, and the stability is lower than that of maleate Form A.

Example 6 Hygroscopicity (DVS) Experiment

Dynamic vapor sorption curves were collected on a DVS Intrinsic by SMS (Surface Measurement Systems).

20 mg sample of the crystal forms of the Examples and Comparative Examples are placed in the environment of 25° C./80% relative humidity for a dynamic vapor sorption (DVS) test, and the test results determined by HPLC are shown in Table 5.

TABLE 5

| Type of salt | Vapor sorption | Hygroscopicity | The crystal form changes after DVS testing or not |
|---|---|---|---|
| Example 1 free base | 0.16% | Almost no hygroscopicity | No |
| Example 2 hydrochloride salt | 0.21% | Almost no hygroscopicity | No |

TABLE 5-continued

| Type of salt | Vapor sorption | Hygroscopicity | The crystal form changes after DVS testing or not |
|---|---|---|---|
| Example 3 sulfate | 0.23% | Slight hygroscopicity | No |
| Example 4 phosphate | 0.61% | Slight hygroscopicity | No |
| Example 5 maleate | 0.12 | Almost no hygroscopicity | No |

The above results show that: within one week, hydrochloride salt, sulfate, phosphate and maleate have almost no hygroscopicity or slight hygroscopicity; Maleate is less hygroscopic than other salts.

Example 7

The in vivo absorption process and characteristics of the free base and four salts thereof (sulfate, hydrochloride salt, phosphate, maleate) of compound (I) in rats were studied. The pharmacokinetics of a single intragastric administration of 1 mg/kg of a compound of Formula I and four salts thereof (calculated by free base concentration in salt form) were studied in SD rats.

Experimental Method

SD rats were given a single intragastric administration of 1 mg/kg free base of Example 1 and four salts thereof (including hydrochloride salt from Example 2, sulfate from Example 3, phosphate from Example 4 and maleate from Example 5). There were 4 male rats in each group. The concentration of the compound of Formula I in plasma was determined, and the pharmacokinetic parameters were calculated according to the concentration-time curve. The results are shown in Table 6.

TABLE 6

Plasma pharmacokinetic parameters in rats after intragastric administration of 1 mg/kg of the free base of compound of Formula I and four salts thereof (Analysis by non-compartmental model) (Mean ± SD, n = 6)

| Drug | $AUC_{0-t}$ ng · h/mL | $AUC_{0-\infty}$ ng · h/mL | $MRT_{0-\infty}$ h | $t_{1/2}$ h | Tmax h | Cmax ng/mL |
|---|---|---|---|---|---|---|
| free base | 137 ± 58.9 | 137 ± 59.0 | 3.63 ± 0.306 | 2.78 ± 0.463 | 0.583 ± 0.289 | 46.6 ± 13.8 |
| Sulfate | 125 ± 28.0 | 125 ± 28.1 | 2.87 ± 0.283 | 2.67 ± 0.267 | 0.417 ± 0.096 | 55.2 ± 3.49 |
| Hydrochloride salt | 96.9 ± 29.3 | 99.1 ± 28.9 | 4.27 ± 2.20 | 4.72 ± 2.66 | 0.625 ± 0.250 | 36.5 ± 13.1 |
| Phosphate | 139 ± 37.1 | 139 + 36.8 | 3.06 ± 0.434 | 3.25 ± 1.23 | 0.833 ± 0.333 | 51.5 ± 16.4 |
| Maleate | 124 ± 5.79 | 125 ± 7.00 | 3.07 ± 0.531 | 4.67 ± 2.17 | 0.750 ± 0.289 | 45.4 ± 2.81 |

As can be seen in Table 6, the maleate has a relatively long half-life, prolongs the time of action in vivo, and is highly bioavailable compared with other salts.

Example 8 In Vivo Individual Difference Analysis of Compound of Formula I and Salts Thereof 1 Material and Method 1.1 Drugs Compound of Formula I and salts thereof (sulfate, hydrochloride salt, phosphate, maleate), supplied by Shanghai Jingxin Biopharmaceutical Co., Ltd.

1.2 Experimental Animal

Strain: SD rats; Gender: male; Body weight: about 250 grams; Source: shanghai Jiesijie Experimental Animal Co., Ltd

1.3 Experimental Method

1.3.1 Administration Method

Route: single intragastric administration; Capacity: measured in 10 mL/kg body weight Preparation: weighing appropriate amount of the free base or salt of the compound of Formula I, adding a small amount of 0.5% CMC-Na to grind, adding 0.5% CMC-Na to the volume. The concentration is measured as the base.

1.3.2 Administration and Sample Collection

20 SD rats were divided into 5 groups with 4 rats in each group, fasted for 12 h and drank freely before administration. Compound of Formula I or salts was given by intragastric administration at the dose of 1 mg/kg respectively. 100 μL of orbital blood samples were collected at 5 min, 10 min, 20 min, 0.5 h, 1 h, 2 h, 4 h, 6 h, 8 h, 12 h, 24 h and 36 h before and after administration. The blood was anticoagulated with 1% heparin, the plasma was separated by 8000 rpm centrifugation for 4 min and stored at −40° C. for testing.

1.4 Plasma Sample Determination Method

LC-MS/MS Method.

1.5 Data Processing

Pharmacokinetic parameters after administration in rats were calculated using a non-compartmental model of DAS 2.0 software.

2 Results

The individual and average plasma concentration-time curves of rats after single intragastric administration of 1 mg/kg compound of Formula I or salts thereof are shown in Table 7(a)-(e) and FIG. 18A-FIG. 18E, respectively; It can be seen that compared with other salts, the individual difference of maleate is the smallest. Small individual differences are of great significance to clinical treatment and avoid the instability of efficacy in the process of clinical application.

TABLE 7a

Plasma Concentrations (ng/mL) of Compound of Formula I after intragastric administration of 1 mg/kg Compound of Formula I to rats

| Time after administration (h) | 1♂ | 2♂ | 3♂ | 4♂ | Mean ± SD |
|---|---|---|---|---|---|
| 0 | 0 | 0 | 0 | 0 | 0.000 ± 0.000 |
| 0.0833 | 0.419 | 0.624 | 12.0 | 0.543 | 3.40 ± 5.74 |
| 0.167 | 6.35 | 11.3 | 25.8 | 16.3 | 14.9 ± 8.30 |
| 0.333 | 26.8 | 33.0 | 51.8 | 57.0 | 42.2 ± 14.5 |
| 0.5 | 33.6 | 37.2 | 51.6 | 63.3 | 46.4 ± 13.7 |
| 1 | 29.4 | 36.3 | 45.6 | 63.6 | 43.7 ± 14.8 |
| 2 | 16.8 | 19.2 | 23.9 | 40.3 | 25.1 ± 10.6 |
| 4 | 5.38 | 6.30 | 7.95 | 16.0 | 8.91 ± 4.85 |
| 6 | 2.03 | 1.94 | 3.06 | 8.91 | 3.99 ± 3.32 |
| 9 | 0.876 | 0.95 | 1.47 | 3.30 | 1.65 ± 1.13 |
| 12 | 0.372 | 0.578 | 0.682 | 1.66 | 0.823 ± 0.573 |
| 24 | 0.487 | 0.308 | 0.886 | 0.306 | 0.497 ± 0.273 |

Note:
part of the 36 h concentration was lower than LLOQ (0.1 ng/mL) and 36 h data are not tabulated.

TABLE 7b

Plasma Concentrations (ng/mL) of Compound of Formula I after intragastric administration of 1 mg/kg the Sulfate of Compound of Formula I to rats

| Time after administration (h) | 1♂ | 2♂ | 3♂ | 4♂ | Mean ± SD |
|---|---|---|---|---|---|
| 0 | 0 | 0 | 0 | 0 | 0.000 ± 0.000 |
| 0.0833 | 1.54 | 2.41 | 2.56 | 2.48 | 2.25 ± 0.476 |
| 0.167 | 24.0 | 18.4 | 23.0 | 21.3 | 21.7 ± 2.45 |
| 0.333 | 50.4 | 54.4 | 51.0 | 48.9 | 51.2 ± 2.32 |
| 0.5 | 56.0 | 36.0 | 48.0 | 59.4 | 49.9 ± 10.4 |
| 1 | 42.6 | 30.0 | 38.5 | 45.8 | 39.2 ± 6.84 |
| 2 | 32.7 | 14.5 | 24.1 | 21.3 | 23.2 ± 7.54 |
| 4 | 10.3 | 4.31 | 10.5 | 6.57 | 7.92 ± 3.01 |
| 6 | 3.08 | 1.35 | 3.99 | 3.05 | 2.87 ± 1.10 |
| 9 | 1.30 | 0.643 | 1.68 | 0.973 | 1.15 ± 0.444 |
| 12 | 0.718 | 0.317 | 0.827 | 0.561 | 0.606 ± 0.221 |
| 24 | 0.213 | 0 135 | 0.148 | 0.479 | 0.244 ± 0.161 |

Note:
part of the 36 h concentration was lower than LLOQ (0.1 ng/mL) and 36 h data are not tabulated.

TABLE 7c

Plasma Concentrations (ng/mL) of Compound of Formula I after intragastric administration of 1 mg/kg the Hydrochloride Salt of Compound of Formula I to rats

| Time after administration (h) | 1♂ | 2♂ | 3♂ | 4♂ | Mean ± SD |
|---|---|---|---|---|---|
| 0 | 0 | 0 | 0 | 0 | 0.000 ± 0.000 |
| 0.0833 | 0.448 | 1.02 | 9.68 | 32.6 | 10.9 ± 15.0 |
| 0.167 | 5.53 | 10.3 | 4.72 | 25.0 | 11.4 ± 9.40 |
| 0.333 | 37.6 | 25.9 | 8.18 | 45.9 | 29.4 ± 16.4 |
| 0.5 | 48.3 | 30.6 | 15.0 | 46.4 | 35.1 ± 15.6 |
| 1 | 32.4 | 25.3 | 20.8 | 42.7 | 30.3 ± 9.55 |
| 2 | 19.4 | 11.5 | 13.3 | 24.3 | 17.1 ± 5.86 |
| 4 | 5.99 | 3.04 | 5.43 | 8.99 | 5.86 ± 2.45 |
| 6 | 2.26 | 1.46 | 2.74 | 3.90 | 2.59 ± 1.02 |
| 9 | 0.932 | 0.683 | 1.32 | 1.25 | 1.05 ± 0.295 |
| 12 | 0.514 | 0.299 | 1.74 | 0.777 | 0.833 ± 0.636 |
| 24 | 0.139 | 0.423 | 0.591 | 0.190 | 0.336 ± 0.210 |

Note:
part of the 36 h concentration was lower than LLOQ (0.1 ng/mL) and 36 h data are not tabulated.

TABLE 7d

Plasma Concentrations (ng/mL) of Compound of Formula I after intragastric administration of 1 mg/kg the Phosphate of Compound of Formula I to rats

| Time after administration (h) | 1♂ | 2♂ | 3♂ | 4♂ | Mean ± SD |
|---|---|---|---|---|---|
| 0 | 0 | 0 | 0 | 0 | 0.000 ± 0.000 |
| 0.0833 | 5.28 | 3.26 | 14.5 | 3.54 | 6.65 ± 5.31 |
| 0.167 | 10.5 | 13.0 | 14.8 | 15.0 | 13.3 ± 2.09 |
| 0.333 | 69.7 | 25.9 | 42.5 | 37.9 | 44.0 ± 18.5 |
| 0.5 | 66.7 | 23.2 | 54.7 | 37.0 | 45.4 ± 19.2 |
| 1 | 51.1 | 34.7 | 60.6 | 40.8 | 46.8 ± 11.4 |
| 2 | 25.9 | 20.0 | 37.2 | 18.2 | 25.3 ± 8.57 |
| 4 | 10.4 | 10.7 | 13.9 | 6.41 | 10.4 ± 3.07 |
| 6 | 3.65 | 3.25 | 5.23 | 2.40 | 3.63 ± 1.19 |
| 9 | 1.45 | 1.61 | 1.89 | 0.978 | 1.48 ± 0.382 |
| 12 | 0.728 | 0.799 | 0.923 | 0.582 | 0.758 ± 0.142 |
| 24 | 0.175 | 0.274 | 0.216 | 0.121 | 0.197 ± 0.0647 |

Note:
part of the 36 h concentration was lower than LLOQ (0.1 ng/mL) and 36 h data are not tabulated.

TABLE 7e

Plasma Concentrations (ng/mL) of Compound of Formula I after intragastric administration of 1 mg/kg the Maleate of Compound of Formula I to rats

| Time after administration (h) | 1♂ | 2♂ | 3♂ | 4♂ | Mean ± SD |
|---|---|---|---|---|---|
| 0 | 0 | 0 | 0 | 0 | 0.000 ± 0.000 |
| 0.0833 | 1.15 | 0.643 | 0.768 | 0.624 | 0.796 ± 0.244 |
| 0.167 | 14.5 | 17.9 | 8.05 | 14.8 | 13.8 ± 4.14 |
| 0.333 | 41.2 | 43.9 | 37.1 | 39.3 | 40.4 ± 2.89 |
| 0.5 | 47.4 | 47.7 | 43.6 | 40.6 | 44.8 ± 3.38 |
| 1 | 45.0 | 44.1 | 44.6 | 41.7 | 43.9 ± 1.48 |
| 2 | 24.4 | 21.8 | 26.7 | 20.1 | 23.3 ± 2.90 |
| 4 | 8.41 | 7.03 | 7.39 | 8.13 | 7.74 ± 0.640 |
| 6 | 3.17 | 2.38 | 2.67 | 2.84 | 2.77 ± 0.330 |
| 9 | 1.32 | 1.02 | 0.998 | 1.38 | 1.18 ± 0.199 |
| 12 | 0.835 | 0.637 | 0.423 | 0.985 | 0.720 ± 0.244 |
| 24 | 0.313 | 0.101 | 0.170 | 0.161 | 0.186 ± 0.0899 |

Note:
part of the 36 h concentration was lower than LLOQ (0.1 ng/mL) and 36 h data are not tabulated.

The invention claimed is:

1. A salt of a cyclohexane derivative N'-[trans-4-[2-[7-(benzo[b]thiophene)-7-piperazinyl]ethyl]cyclohexyl]-N,N-dimethylurea of Formula I, wherein the salt comprises an anion, and the anion is a maleate ion,

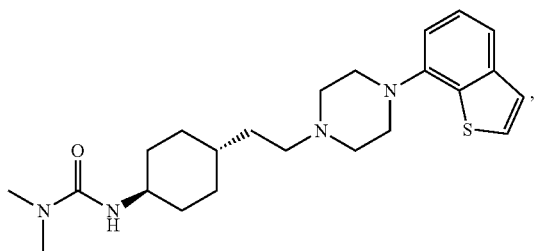

Formula I the stoichiometric ratio of the compound of Formula I to the anion is 1:1, wherein the X-ray powder diffraction pattern of the salt, expressed in 2θ angle by using Cu-Kα radiation, has diffraction peaks at least at 11.804°±0.2°, 12.703°±0.2°, 13.493°±0.2°, 14.495°±0.2°, 15.096°±0.2°, 17.108°±0.2°, 19.104°±0.2° 19.655°±0.2°, 20.023°±0.2°, 21.6110±0.20 and 24.0880±0.20.

2. The salt of claim 1, wherein the salt also has diffraction peaks at 2θ values of 7.246°±0.2°, 17.567°±0.2°, 18.794°±0.2°, 20.395°±0.2°, 21.030°±0.2°, 22.496°±0.2°, 24.867°±0.2° and 26.412°±0.2°.

3. The salt of claim 2, wherein the salt also has diffraction peaks at 2θ values of 11.045°±0.2°, 22.997°±0.2°, 25.336°±0.2°, 27.786°±0.2°, 28.292°±0.2°, 28.914°±0.2°, 29.804°±0.2°, 30.770°±0.2°, 31.628°±0.2° and 33.952°±0.2°.

4. The salt of claim 1, wherein in DSC analysis, the salt has an endothermic peak at 191.8° C.; in TGA analysis, the weight loss reaches 0.41% at 150° C.

5. A pharmaceutical composition for the treatment or amelioration of schizophrenia or bipolar disorders, wherein the pharmaceutical composition comprises the salt of claim 1 and pharmaceutically acceptable auxiliaries.

6. The salt of claim 3, wherein the salt has an XRPD pattern as shown in FIG. 5A.

7. The salt of claim 4, wherein the DSC pattern is as shown in FIG. 5B.

8. The salt of claim 4, wherein the TGA pattern is as shown in FIG. 5C.

* * * * *